(12) United States Patent
Shirakata et al.

(10) Patent No.: US 8,467,726 B2
(45) Date of Patent: Jun. 18, 2013

(54) COMMUNICATION DEVICE AND COMMUNICATION METHOD

(75) Inventors: Naganori Shirakata, Kanagawa (JP); Koji Imamura, Eindhoven (NL); Yoshitaka Ohta, Osaka (JP)

(73) Assignee: Panasonic Corporation, Osaka (JP)

( * ) Notice: Subject to any disclaimer, the term of this patent is extended or adjusted under 35 U.S.C. 154(b) by 206 days.

(21) Appl. No.: 13/144,565

(22) PCT Filed: Aug. 25, 2010

(86) PCT No.: PCT/JP2010/005227
§ 371 (c)(1),
(2), (4) Date: Jul. 14, 2011

(87) PCT Pub. No.: WO2011/055477
PCT Pub. Date: May 12, 2011

(65) Prior Publication Data
US 2011/0294429 A1    Dec. 1, 2011

(30) Foreign Application Priority Data

Nov. 6, 2009    (JP) ................................ 2009-254656

(51) Int. Cl.
*H04B 7/00* (2006.01)

(52) U.S. Cl.
USPC ... 455/41.2; 455/41.1; 455/67.11; 455/67.13; 455/556.1; 455/556.2; 455/99; 455/100; 455/522; 455/574; 455/456.1; 455/456.4; 455/500; 455/502; 455/507; 340/539.1; 340/539.11; 340/539.12; 340/539.13; 340/539.22; 340/539.23; 340/539.26; 340/539.3; 600/300; 600/301

(58) Field of Classification Search
USPC ............... 455/41.1, 41.2, 67.11, 67.13, 68, 455/69, 556.1, 556.2, 91, 99, 100, 522, 574, 455/3.05, 3.06, 414.1, 414.2, 456.1, 456.3, 455/456.4, 456.6, 500, 502, 507; 340/539.1, 340/539.11–539.19, 539.2, 539.21–539.29, 340/539.3; 600/300, 301
See application file for complete search history.

(56) References Cited

U.S. PATENT DOCUMENTS 6,225,901 B1 * 5/2001 Kail, IV .................. 340/539.11
6,315,719 B1   11/2001 Rode et al.
(Continued)

FOREIGN PATENT DOCUMENTS

| JP | 11-098574 | 4/1999 |
|----|-----------|--------|
| JP | 2001-057966 | 3/2001 |
| JP | 2003-318999 | 11/2003 |
| JP | 2004-065803 | 3/2004 |
| JP | 2008-073456 | 4/2008 |

OTHER PUBLICATIONS

International Search Report issued Sep. 28, 2010 in International (PCT) Application No. PCT/JP2010/005227.

(Continued)

*Primary Examiner* — Tuan A Tran
(74) *Attorney, Agent, or Firm* — Wenderoth, Lind & Ponack, L.L.P.

(57) ABSTRACT

The communication device (10) which performs, when attached to the first region of the moving body, wireless communication with the communication partner device (20) attached to the second region of the moving body includes: a motion obtaining unit (11) which obtains motion information indicating a motion of at least one region of the moving body; a parameter determining unit (12) which determines a parameter corresponding to the motion of the region of the moving body indicated by the motion information obtained by the motion obtaining unit (11), using parameter information in which the motion and a parameter indicating a communication mode for successful wireless communication are associated with each other; and a wireless communication unit (13) which performs wireless communication with the communication partner device (20) according to the parameter determined by the parameter determining unit (12).

14 Claims, 22 Drawing Sheets

U.S. PATENT DOCUMENTS

| | | |
|---|---|---|
| 6,542,471 B1 | 4/2003 | Ito |
| 6,549,756 B1* | 4/2003 | Engstrom .................... 455/66.1 |
| 6,621,413 B1* | 9/2003 | Roman et al. ............ 340/539.12 |
| 6,992,580 B2* | 1/2006 | Kotzin et al. ............ 340/539.11 |
| 7,248,894 B2* | 7/2007 | Fujieda et al. ................ 455/557 |
| 7,957,767 B2* | 6/2011 | Rofougaran ............... 455/556.1 |
| 8,085,145 B2* | 12/2011 | Fu et al. .................... 340/539.22 |
| 8,195,229 B2* | 6/2012 | Rofougaran ................ 455/556.1 |
| 2005/0197063 A1* | 9/2005 | White .......................... 455/41.2 |
| 2006/0094449 A1* | 5/2006 | Goldberg .................. 455/456.6 |
| 2006/0240865 A1* | 10/2006 | White ........................ 455/552.1 |
| 2008/0076978 A1 | 3/2008 | Ouchi et al. |
| 2010/0056116 A1* | 3/2010 | Kim et al. .................. 455/414.1 |

OTHER PUBLICATIONS

M. Kuroda et al., "Empirical Evaluation of Zero-admin Authentication for Vital Sensors in Body Area Networks", 30$^{th}$ Annual International IEEE EMBS Conferences, Aug. 20-24, 2008, pp. 2349-2352.

A. Volmer et al., "Wireless Body Sensor Network for Low-Power Motion-Tolerant Syncronized Vital Sign Measurement", 30$^{th}$ Annual International IEEE EMBS Conferences, Aug. 20-24, 2008, pp. 3422-3425.

* cited by examiner

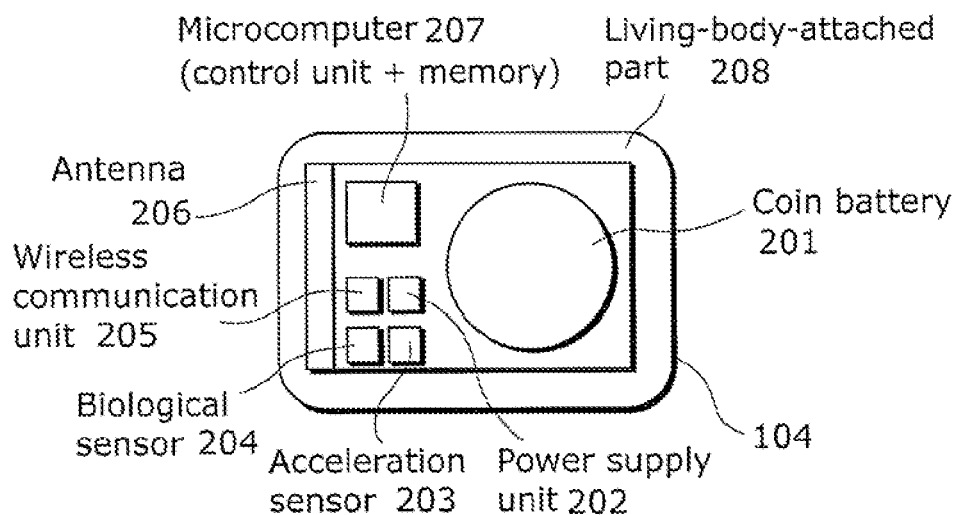
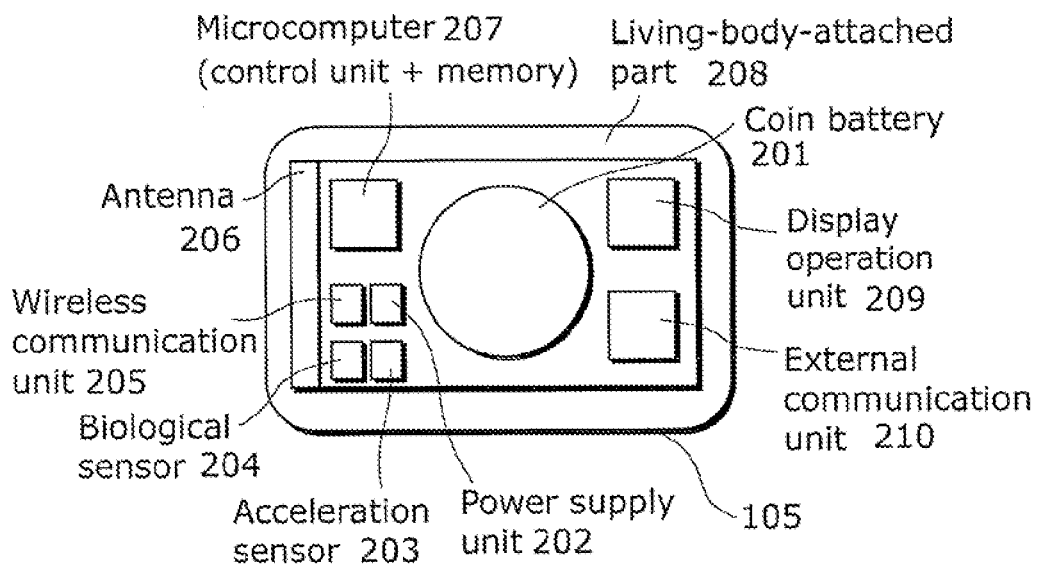

FIG. 17

| Motion information | Reception strength | Transmission timing | Transmission power | Retransmission |
|---|---|---|---|---|
| HMM | H | now | ±0 | now |
| MHM | H | now | ±0 | now |
| MMH | L | delay | H | 2T |
| MMM | L | delay | H | 1T |
| LMM | H | now | ±0 | now |
| HLM | H | now | ±0 | now |
| LHL | H | now | ±0 | now |
| MLH | L | delay | H | 2T |
| MML | M | now/delay | M | 1T |

FIG. 19

| Motion information | Reception strength | Transmission timing | Transmission power | Retransmission |
|---|---|---|---|---|
| HMM | H | now | ±0 | now |
| MHM | H | now | ±0 | now |
| MMH | L | delay | H | 2T |
| MMM | L | delay | H | 1T |
| LMM | H | now | ±0 | now |
| HLM | H | now | ±0 | now |
| Communication failure (NG) → LHL | H → L | now → delay | ±0 → H | now → 2T |
| MLH | L | delay | H | 2T |
| MML | M | now/delay | M | 1T |

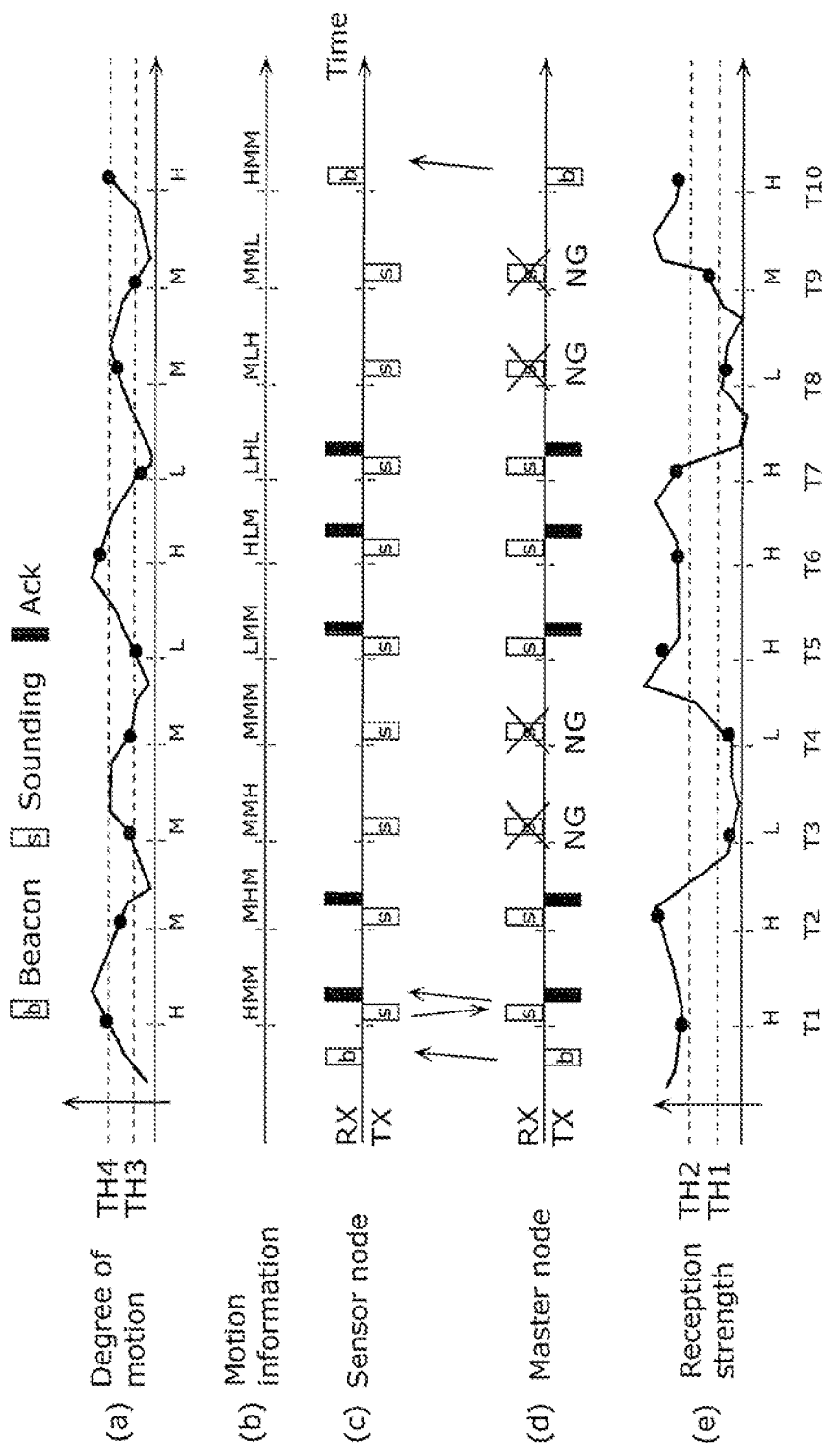

FIG. 21A

| Motion information | Result of transmission | Transmission timing | Transmission power | Retransmission |
|---|---|---|---|---|
| HMM | OK | now | ±0 | now |
| MHM | OK | now | ±0 | now |
| MMH | NG | delay | H | 2T |
| MMM | NG | delay | H | 1T |
| LMM | OK | now | ±0 | now |
| HLM | OK | now | ±0 | now |
| LHL | OK | now | ±0 | now |
| MLH | NG | delay | H | 2T |
| MML | NG | delay | H | 1T |

FIG. 21B

| Motion information | Reception strength | Transmission timing | Transmission power | Retransmission |
|---|---|---|---|---|
| HMM | H | now | ±0 | now |
| MHM | H | now | ±0 | now |
| XXX→XMH→MMH | L | delay | H | 2T |
| XXX→XXM→MMM | L | delay | H | 1T |
| LMM | H | now | ±0 | now |
| HLM | H | now | ±0 | now |
| LHL | L | delay | H | 2T |
| MLH | M | now/delay | M | 1T |
| MML | | | | |

COMMUNICATION DEVICE AND COMMUNICATION METHOD

TECHNICAL FIELD

The present invention relates to a communication device which performs, when attached to a region of a moving body, wireless communication with a communication partner device attached to another region of the moving body.

BACKGROUND ART

In recent years, much attention has been given to systems which perform health management or medical diagnosis support by constantly measuring biological information without restricting movements of users in daily life. In order to perform such measuring, measuring devices are required which have no inconvenience of wiring, are compact, and consume low power.

In a conventional biological information measuring system, an external device (information terminal) collects, through wireless communication, biological information measured by a sensor (measuring device) measuring biological information (e.g., refer to PTL 1).

The biological information measuring system disclosed in PTL 1 includes: an information terminal which is provided at a predetermined position and collects biological information; and a measuring device which is attached to a living body and measures biological information.

The measuring device measures pulse data and acceleration data as the biological information, and automatically transmits, through wireless communication, the measured biological information to the information terminal. Here, when the measuring device and the information terminal remain always wirelessly communicable with each other, there is a problem of increasing power consumption of especially the measuring device.

In response, according to a technique disclosed in PTL 1, it is detected whether or not the measuring device has moved, using the acceleration data. Then, a transmission timing for the biological information is controlled based on whether or not the measuring device has moved and has previously been communicable. Such controlling of the transmission timing for the biological information makes it possible to reduce wireless communication power consumption.

CITATION LIST

Patent Literature

[PTL 1]
Japanese Unexamined Patent Application Publication No. 2008-73456

SUMMARY OF INVENTION

Technical Problem

When pieces of various biological information (e.g., body temperature, heartbeat, blood pressure, cardiac electric activity, myoelectric activity, and blood oxygen saturation level) of a living body such as a person are measured while the living body is in action, each of measuring devices needs to be attached to one of regions suitable for measuring a corresponding one of the pieces of biological information. In the above conventional technique, when the measuring devices are attached to different regions of the living body, each of the measuring devices individually communicates with the information terminal. As a result, communication power consumption of each measuring device is increased.

In response, a configuration can be considered in which a piece of data of each measuring device is temporarily brought to a relay device, and the pieces of data temporarily brought to the relay device are transmitted to the information terminal. In this case, each measuring device performs wireless communication with the replay device attached to a region (e.g., chest) of the living body, and thus it is possible to decrease a communication distance and reduce the communication power consumption.

However, in the wireless communication between the devices attached to the living body, a radio propagation environment is significantly varied under the influence of living tissue or a change in position by a movement of the living body. For this reason, even though the communication distance is decreased by attaching the relay device to the living body, communication between each measuring device and the relay device becomes unstable.

Moreover, there is a case where the radio propagation environment between the measuring device and the relay device is varied when, though a region (e.g., a head region) to which a measuring device to be communicated with is attached is not moving, another region (e.g., an arm region) moves, and accordingly a communication status is changed.

In such a case, the technique disclosed in PTL 1 in which it is judged possible to communicate with the measuring device if the measuring device is not moving when the measuring device is previously communicable does not enable reliable wireless communication.

The present invention is conceived to solve the above problems, and has an object of providing a communication device which makes it possible to increase reliability in wireless communication between the communication device attached to a first region of a moving body and a communication partner device attached to a second region of the moving body, and to reduce wireless communication power consumption.

Solution to Problem

In order to achieve the above object, a communication device according to an aspect of the present invention is a communication device which performs, when attached to a first region of a moving body, wireless communication with a communication partner device attached to a second region of the moving body, the communication device including: a motion obtaining unit configured to obtain motion information indicating a motion of at least one region of the moving body; a parameter determining unit configured to determine a parameter corresponding to the motion of the region of the moving body indicated by the motion information obtained by the motion obtaining unit, using parameter information in which the motion and a parameter indicating a communication mode for successful wireless communication are associated with each other; and a wireless communication unit configured to perform wireless communication with the communication partner device according to the parameter determined by the parameter determining unit.

With this configuration, it is possible to determine the parameter indicating the communication mode for successful wireless communication between the communication device and the communication partner device, based on the motion of the region influencing the radio propagation environment between the communication device and the communication partner device. Thus, it is possible to effectively determine the parameter adapted to the current or future radio propagation environment. Performing wireless communication according to the parameter thus determined makes it possible to increase the reliability in wireless communication, and reduce the wireless communication power consumption.

Moreover, it is preferred that the motion obtaining unit obtains, as the motion information, information indicating a motion of the first region, and that the parameter information is information in which the motion of the first region and the parameter are associated with each other.

With this configuration, when the motion of the first region to which the communication device is attached influences the radio propagation environment between the communication device and the communication partner device, it is possible to effectively determine the parameter.

Moreover, it is preferred that the wireless communication unit receives a radio signal from the communication partner device, and that the communication device further includes a parameter generating unit which generates the parameter information in which a parameter corresponding to signal strength of the received radio signal and the motion of the first region indicated by the motion information obtained when the radio signal is received are associated with each other.

With this configuration, it is possible to generate the parameter information used in determining the parameter, using the signal strength of the radio signal actually received. In other words, it is possible to dynamically generate the parameter information according to the dependence relationship between the motion of the first region to which the communication device is attached and the radio propagation environment between the communication device and the communication partner device. Therefore, determining the parameter using the parameter information thus generated makes it possible to increase the reliability in wireless communication, and reduce the wireless communication power consumption.

Moreover, it is preferred that the motion obtaining unit obtains, as the motion information, information indicating a motion of the second region, and that the parameter information is information in which the motion of the second region and the parameter are associated with each other.

With this configuration, when the motion of the second region to which the communication partner device is attached influences the radio propagation environment between the communication device and the communication partner device, it is possible to effectively determine the parameter.

Moreover, it is preferred that wireless communication unit receives a radio signal including the motion information indicating the motion of the second region from the communication partner device, and that the communication device further includes a parameter generating unit which generates the parameter information in which a parameter corresponding to signal strength of the received radio signal and the motion of the second region indicated by the motion information obtained when the radio signal is received are associated with each other.

With this configuration, it is possible to generate the parameter information used in determining the parameter, using the signal strength of the radio signal actually received. In other words, it is possible to dynamically generate the parameter information according to the dependence relationship between the motion of the second region to which the communication partner device is attached and the radio propagation environment between the communication device and the communication partner device. Therefore, determining the parameter using the parameter information thus generated makes it possible to increase the reliability in wireless communication, and reduce the wireless communication power consumption.

Moreover, it is preferred that a motion measuring device which measures a motion of a third region that is different from the first and second regions is attached to the third region, that the motion obtaining unit obtains, as the motion information, information indicating the motion of the third region from the motion measuring device, and that the parameter information is information in which the motion of the third region and the parameter are associated with each other.

With this configuration, when the motion of the third region to which the motion measuring device is attached influences the radio propagation environment between the communication device and the communication partner device, it is possible to effectively determine the parameter.

Moreover, it is preferred that wireless communication unit receives a radio signal from the communication partner device, and a radio signal including motion information indicating the motion of the third region from the motion measuring device, and that the communication device further includes a parameter generating unit which generates the parameter information in which a parameter corresponding to signal strength of the radio signal received from the communication partner device and the motion information included in the radio signal received from the motion measuring device are associated with each other.

With this configuration, it is possible to generate the parameter information used in determining the parameter, using the signal strength of the radio signal actually received. In other words, it is possible to dynamically generate the parameter information according to the dependence relationship between the motion of the third region to which the motion measuring device is attached and the radio propagation environment between the communication device and the communication partner device. Therefore, determining the parameter using the parameter information thus generated makes it possible to increase the reliability in wireless communication, and reduce the wireless communication power consumption.

Moreover, it is preferred that the motion information is information indicating a temporal variation in magnitude of acceleration of the region of the moving body.

With this configuration, it is possible to easily obtain the motion information using the acceleration sensor.

Moreover, it is preferred that the parameter includes at least one of a parameter for specifying communication timing and a parameter for specifying radio wave strength in transmission.

With this configuration, it is possible to control the at least one of the transmission timing and the radio wave strength in transmission, and thus it is possible to effectively reduce the wireless communication power consumption.

Moreover, it is preferred that the communication device further includes a moving body information sensor which measures moving body information of the first region, wherein the wireless communication unit transmits, through wireless communication, the moving body information measured by the moving body information sensor, to the communication partner device.

With this configuration, it is possible to transmit, to the communication partner device, the moving body information measured by the communication device.

Moreover, it is preferred that the communication partner device measures moving body information of the second region, and that the wireless communication unit receives, through wireless communication, the moving body information measured by the communication partner device.

With this configuration, it is possible to collect the moving body information measured by the communication partner device.

Moreover, it is preferred that there is more than one communication partner device, and that the communication device further includes an external communication unit which transmits, to an external device not attached to the moving body, the moving body information which the wireless communication unit has received from each of the communication partner devices.

With this configuration, it is possible to collect the moving body information measured by the communication partner device, and transmit the collected moving body information to the external device. This eliminates the need for each communication partner device to communicate with a remote external device, and thus it is possible to reduce power consumption as a whole system.

The present invention can be realized not only as the communication device including such characteristic processing units but also as a communication method including, as steps, the characteristic processing units of the communication device. In addition, the present invention can be realized as a computer program causing a computer to execute each characteristic step included in the communication method. It goes without saying that such a computer program can be distributed via non-transitory computer-readable recording medium such as a CD-ROM (Compact Disc Read Only Memory) or a communication network such as the Internet.

Additionally, the present invention can be realized as an integrated circuit including the characteristic processing units included in the communication device.

Advantageous Effects of Invention

The present invention makes it possible to effectively determine a parameter adapted to a current or future radio propagation environment, thereby increasing reliability in wireless communication and reducing wireless communication power consumption.

BRIEF DESCRIPTION OF DRAWINGS

FIG. 9A is a schematic diagram showing a hardware configuration of a sensor node according to Embodiment 4 of the present invention.

FIG. 9B is a schematic diagram showing a hardware configuration of a master node according to Embodiment 4 of the present invention.

FIG. 17 is a diagram showing an example of the transmission parameter table according to Embodiment 4 of the present invention.

FIG. 19 is a diagram showing an example where the sensor node updates the transmission parameter table according to Embodiment 4 of the present invention.

FIG. 20 is a diagram showing an exemplary sequence through which a sensor node creates a transmission parameter table according to Embodiment 5 of the present invention.

FIG. 21A is a diagram showing an example of the transmission parameter table created by the sensor node according to Embodiment 5 of the present invention.

FIG. 21B is a diagram showing an example of the transmission parameter table created by the master node according to Embodiment 5 of the present invention.

DESCRIPTION OF EMBODIMENTS

The following describes embodiments of the present invention with reference to the drawings. For the sake of convenience of description, each of the embodiments describes a case where a living body is a person. It is to be noted that the living body does not always have to be the person, and may be any moving body with motor ability such as a mouse, a monkey, and a dog.

Embodiment 1

The following first describes Embodiment 1 of the present invention.

A communication device according to this embodiment determines a parameter for successful wireless communication between the communication device and a communication partner device, using dependence of a radio propagation environment between the communication device and the communication partner device (hereinafter, simply referred to as a "radio propagation environment") on motion information indicating a motion of a first region to which the communication device is attached.

Figure 1:
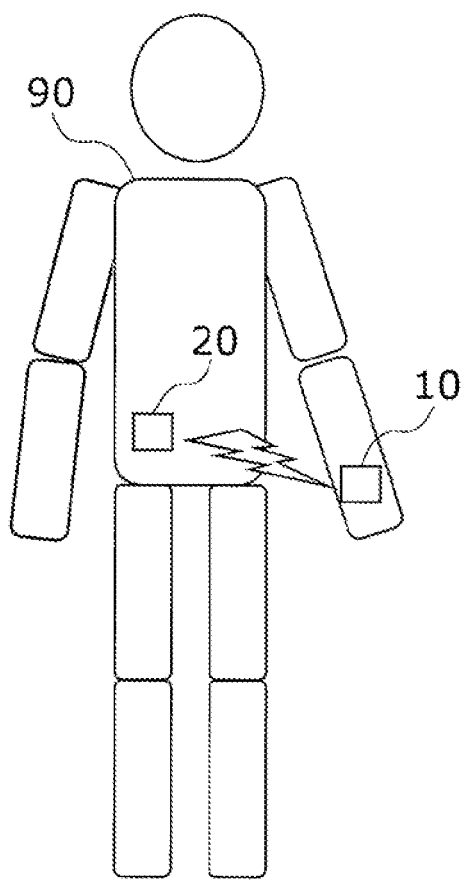
FIG. 1 is a diagram showing an overview of a communication system according to Embodiment 1 of the present invention.

FIG. 1 is a diagram showing an overview of a communication system 1 according to Embodiment 1 of the present invention. As shown in FIG. 1, the communication system 1 includes a communication device 10 and a communication partner device 20.

The communication device 10 is attached to a first region of a person 90, and performs, when attached to the first region, wireless communication with the communication partner device 20 attached to a second region of the person 90. The first region is one of regions of the person 90 such as a hand region, an arm region, a leg region, a lower back region, a chest region, and a head region. In this embodiment, the motion of the first region significantly influences the radio propagation environment. In other words, the radio propagation environment depends on the motion of the first region.

The communication partner device 20 is attached to a second region of the person 90, and performs, when attached to the second region, wireless communication with the communication device 10 attached to the first region. The second region is one of the regions of the person 90, and is different from the first region.

Figure 2:
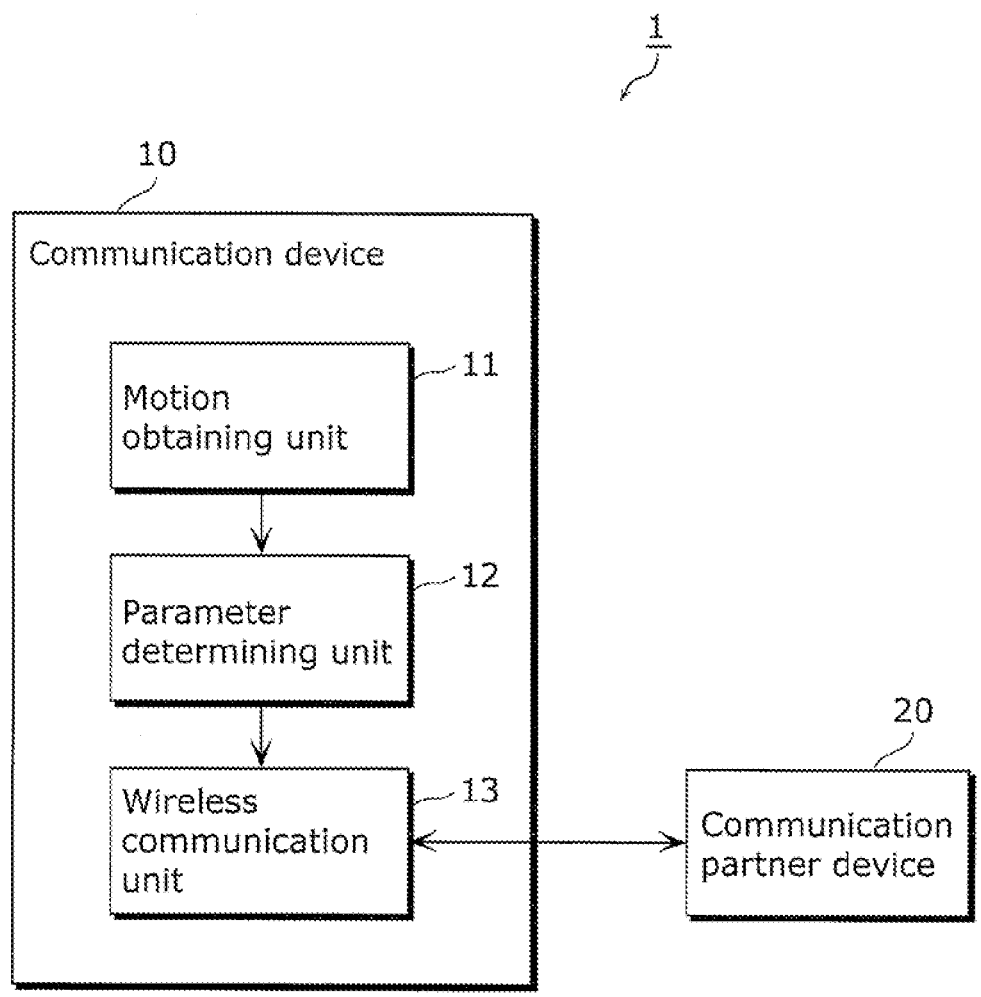
FIG. 2 is a block diagram showing a functional configuration of the communication system according to Embodiment 1 of the present invention.

FIG. 2 is a block diagram showing a functional configuration of the communication system 1 according to Embodiment 1 of the present invention. As shown in FIG. 2, the communication device 10 includes a motion obtaining unit 11, a parameter determining unit 12, and a wireless communication unit 13.

The motion obtaining unit 11 obtains motion information indicating a motion of at least one region of a living body. Here, the motion information is information indicating a motion of a region influencing the radio propagation environment. More specifically, the motion information is, for instance, information indicating a temporal variation in magnitude of acceleration of the region of the living body. It is to be noted that the motion information is not necessarily the information indicating the temporal variation in magnitude of acceleration of the region of the living body.

In this embodiment, the motion obtaining unit 11 obtains information indicating the motion of the first region as the motion information. More specifically, the motion obtaining unit 11 includes, for example, a sensor (e.g., a gyroscope, an acceleration sensor, or a position sensor) which detects the motion of the first region.

The parameter determining unit 12 determines a parameter corresponding to the motion indicated by the motion information obtained by the motion obtaining unit 11, using parameter information. Here, the parameter information is information in which the motion of the region of the living body and a parameter indicating a communication mode for successful wireless communication are associated with each other. For instance, the parameter information is a table in which the motion of the region of the living body and the parameter are associated with each other or a numerical expression.

It is to be noted that, in this embodiment, the parameter information is the information in which the motion of the region of the living body and the parameter are associated with each other. In other words, the parameter determining unit 12 determines a parameter adapted to a current or future radio propagation environment, taking advantage of the significant influence of the motion of the first region on the radio propagation environment.

Here, the parameter indicates a communication mode at a time when wireless communication is performed between the communication device 10 and the communication partner device 20. More specifically, the parameter is, for instance, a parameter relating to modulation method, data rate, error-correction coding, transmission timing, transmission power, directivity control, or relay route. More preferably, the parameter includes at least one of a parameter for specifying a transmission timing and a parameter for specifying radio wave strength in transmission (transmission power). With this, the communication device 10 successfully controls the at least one of the transmission timing and the radio wave strength in transmission, and thus makes it possible to effectively reduce wireless communication power consumption.

The wireless communication unit 13 performs wireless communication with the communication partner device 20 attached to the second region, according to the determined parameter. More specifically, the wireless communication unit 13 transmits, for example, biological information or the like measured by the communication device 10, to the communication partner device 20, according to the parameter.

Moreover, for instance, the wireless communication unit 13 may transmit a radio signal including the determined parameter, to the communication partner device 20. In this case, the communication partner device 20 transmits data (e.g., the biological information measured by the communication partner device 20) to the communication device 10, according to the parameter included in the received radio signal.

It is to be noted that the wireless communication unit 13 may be configured by commonly-used constituent, elements necessary for wireless communication, and may be configured by, for instance, a circuit for modulating data and the like.

Figure 3:
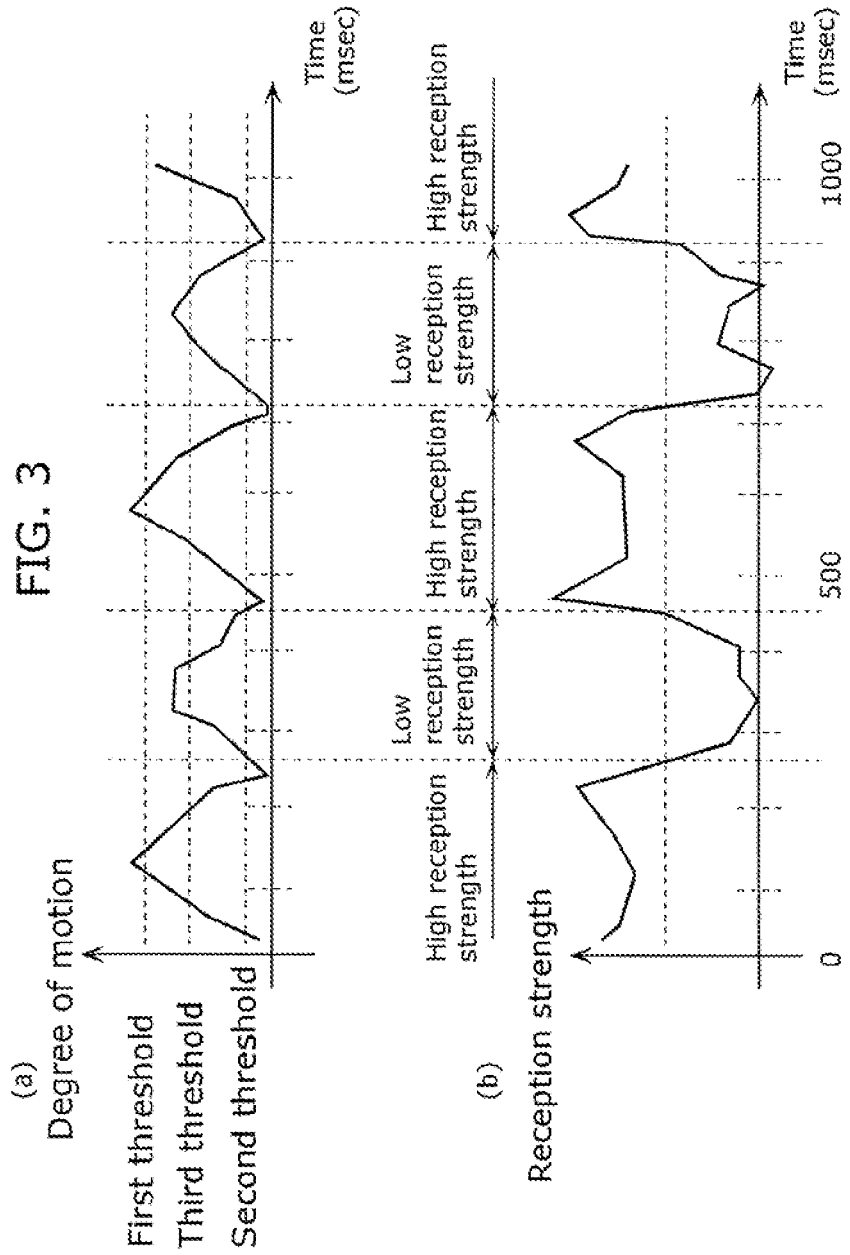
FIG. 3 is a diagram illustrating an influence of a motion of a region of a living body on a radio propagation environment.

The following describes the influence of the motion of the region on the radio propagation environment with reference to FIG. 3.

FIG. 3 is a diagram illustrating an influence of a motion of a region of a living body on a radio propagation environment. More specifically, (a) in FIG. 3 is a graph showing a temporal variation in degree of motion of an arm region of a walking person. Moreover, (b) in FIG. 3 is a graph showing a temporal variation in reception strength of a radio signal between the communication device 10 attached to the arm region and the communication partner device 20 attached to a lower back region of the person.

The degree of motion indicates magnitude of acceleration of the arm region measured by the communication device 10.

The reception strength indicates signal strength of a signal received by one of the communication device 10 and the communication partner device 20. In other words, the reception strength indicates radio field strength at a time when one of the communication device 10 and the communication partner device 20 receives radio waves emitted with predetermined strength by the other one of the communication device 10 and the communication partner device 20. The greater the reception strength is, the better the radio propagation environment is.

As shown in FIG. 3, in a time interval in which a temporal variation in degree of motion is represented by a relatively large convex shape, the reception strength is increased, and the radio propagation environment becomes favorable. In contrast, in a time interval showing a temporal variation in which a degree of motion is represented by a relatively small convex shape, the reception strength is decreased, and the radio propagation environment becomes unfavorable. Such a relationship between the degree of motion and the reception strength is repeated, and is reproducible.

Accordingly, it is clear that the motion of the arm region influences the radio propagation environment. In other words, it is clear that the radio propagation environment depends on the motion of the arm region.

Thus, using such dependence of the reception strength on the temporal variation in degree of motion makes it possible to determine a parameter adapted to current or future reception strength, based on the degree of motion. To put it differently, using the dependence of the radio propagation environment on the motion information makes it possible to determine the parameter for successful wireless communication, based on the motion information.

More specifically, for instance, the parameter determining unit 12 may determine a parameter that is wirelessly communicable even when the radio propagation environment is deteriorated, as a parameter corresponding to motion information indicating that a degree of motion equal to or less than a second threshold value is to be measured after a degree of motion equal to or greater than a first threshold value is measured as a local maximum. Moreover, for example, the parameter determining unit 12 may determine a parameter to be used when the radio propagation environment is favorable, as a parameter corresponding to the motion information indicating that the degree of motion equal to or less than the second threshold value is to be measured after a degree of motion equal to or greater than a third threshold value and less than the first threshold value is measured as the local maximum.

Stated differently, the communication device 10 determines the parameter using the parameter information generated in advance by taking advantage of the dependence of the radio propagation environment on the motion information, and thus makes it possible to perform wireless communication using the parameter adapted to the current or future radio propagation environment. It is to be noted that what kind of the dependence of the radio propagation environment (reception strength) on the motion information may be estimated by a person with an ordinary skill in the art based on a commonly-known statistical method or the like. The parameter information may be generated using the motion information thus estimated.

It is to be noted that although the case where the motion information indicates the temporal variation in degree of motion is described in FIG. 3, the motion information does not necessarily indicate the temporal variation in degree of motion. For instance, the motion information may indicate a temporal variation in motion direction. Moreover, the motion information may indicate a temporal variation in degree or direction of relative motion between the regions. Moreover, the motion information may be plural in number. In other words, the motion information may be at least one information indicating a motion of a region influencing the radio propagation environment between the communication device 10 and the communication partner device 20.

The following briefly describes each type of operation performed by the communication device 10 thus configured.

Figure 4:
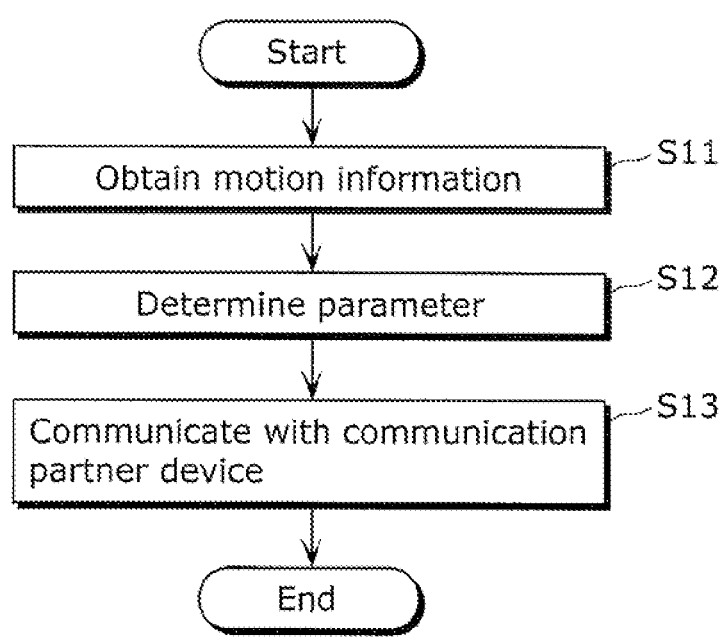
FIG. 4 is a flowchart showing a flow of processing performed by a communication device according to Embodiment 1 of the present invention.

FIG. 4 is a flowchart showing a flow of processing performed by the communication device 10 according to Embodiment 1 of the present invention.

First, the motion obtaining unit 11 obtains motion information indicating a motion of at least one region of a living body (S11). Next, the parameter determining unit 12 determines a parameter corresponding to a motion indicated by the motion information obtained by the motion obtaining unit 11, using parameter information in which the motion of the region of the living body and a parameter indicating a communication mode for successful wireless communication are associated with each other (S12).

Then, the wireless communication unit 13 performs wireless communication with the communication partner device 20 attached to a second region of the living body, according to the determined parameter (S13).

As described above, the communication device 10 according to this embodiment makes it possible to determine the parameter indicating the communication mode for successful wireless communication between the communication device 10 and the communication partner device 20, based on the motion of the first region influencing the radio propagation environment between the communication device 10 and the communication partner device 20. Therefore, the communication device 10 makes it possible to effectively determine the parameter adapted to the current or future radio propagation environment. In addition, the communication device 10 increases the reliability in wireless communication by performing wireless communication according to the parameter thus determined, and makes it possible to reduce the wireless communication power consumption.

Moreover, the communication device 10 according to this embodiment makes it possible to effectively determine the parameter regardless of the degree of motion of the first region at a certain point.

Embodiment 2

The following describes Embodiment 2 of the present invention.

The communication device according to Embodiment 1 determines the parameter for successful wireless communication with the communication partner device attached to the second region, based on the motion information indicating the motion of the first region to which the communication device is attached. However, when the influence of the motion of the first region on the radio propagation environment is little, the communication device has difficulty determining the parameter adapted to the current or future radio propagation environment, using the motion information indicating the motion of the first region.

In response, a communication device according to this embodiment determines a parameter for successful wireless communication, based on motion information indicating a motion of the second region to which a communication partner device is attached. The following describes the communication device according to this embodiment, mainly centering around differences from Embodiment 1.

Figure 5:
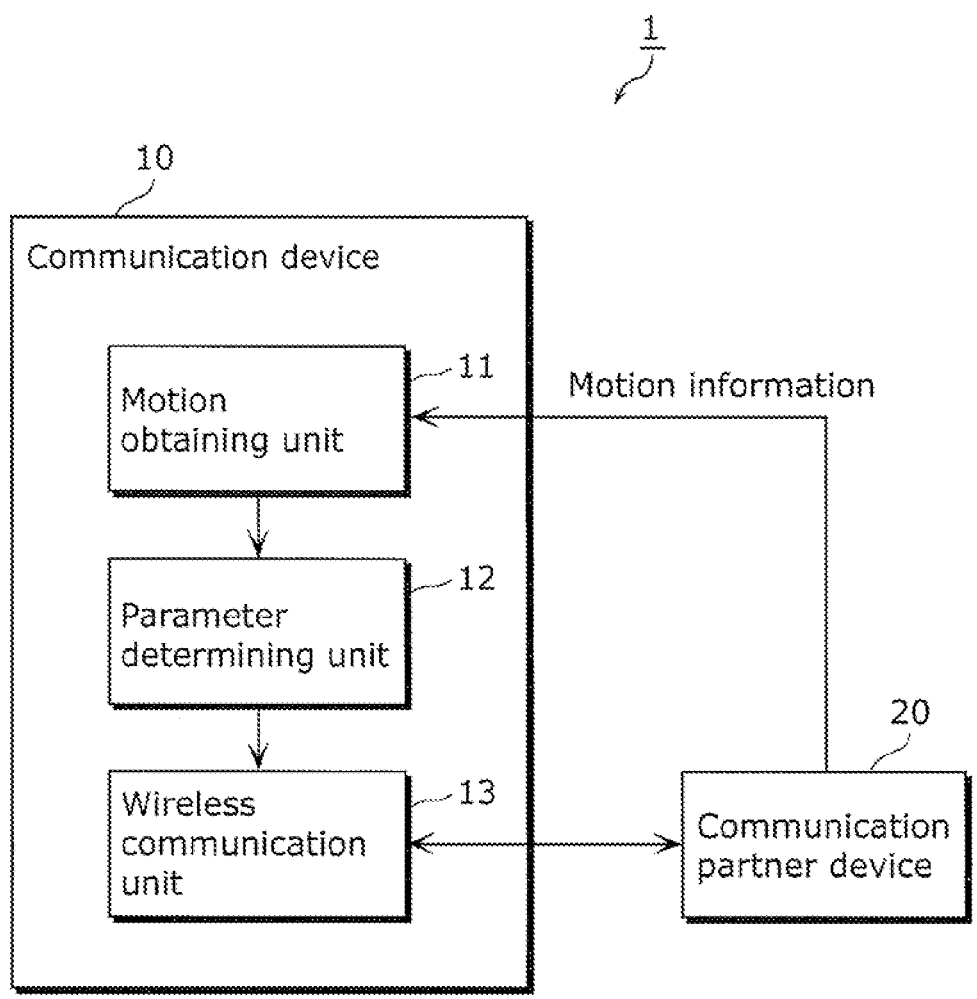
FIG. 5 is a block diagram showing a functional configuration of a communication system according to Embodiment 2 of the present invention.

FIG. 5 is a block diagram showing a functional configuration of a communication system 1 according to Embodiment 2 of the present invention. The wireless communication unit 13 in FIG. 5 is the same as in FIG. 2, and thus a description thereof is omitted. In addition, each type of operation performed by the communication device 10 is the same as in FIG. 4, and thus a diagrammatic representation and description thereof are omitted.

The motion obtaining unit 11 obtains, from the communication partner device 20, information indicating the motion of the second region as motion information. More specifically, the motion obtaining unit 11 obtains, through wireless communication, the information indicating the motion of the second region measured by the communication partner device 20, from the communication partner device 20.

It is to be noted that, in this embodiment, the motion of the second region significantly influences the radio propagation environment. In other words, the radio propagation environment depends on the motion of the second region.

The parameter determining unit 12 determines a parameter corresponding to the motion indicated by the motion information obtained by the motion obtaining unit 11, using parameter information. In this embodiment, the parameter information is information in which the motion of the second region and the parameter are associated with each other. In other words, the parameter determining unit 12 determines a parameter adapted to a current or future radio propagation environment, by taking advantage of the significant influence of the motion of the second region on the radio propagation environment.

As described above, the communication device 10 according to this embodiment makes it possible to determine the parameter indicating a communication mode for successful wireless communication between the communication device 10 and the communication partner device 20, based on the motion of the second region influencing the radio propagation environment between the communication device 10 and the communication partner device 20. Therefore, when the motion of the second region to which the communication partner device 20 is attached influences the radio propagation environment, the communication device 10 makes it possible to effectively determine the parameter adapted to the current or future radio propagation environment. In addition, the communication device 10 increases the reliability in wireless communication by performing wireless communication according to the parameter thus determined, and makes it possible to reduce the wireless communication power consumption.

Embodiment 3

The following describes Embodiment 3 of the present invention.

The communication device according to Embodiment 1 or 2 determines the parameter for successful wireless communication with the communication partner device, based on the motion information indicating the motion of the first region to which the communication device is attached or the second region to which the communication partner device is attached, respectively. However, when the influence of the motion of the first region or the second region on the radio propagation environment is little, the communication device has difficulty determining the parameter adapted to the current or future radio propagation environment, using the motion information indicating the motion of the first region or the second region.

In response, a communication device according to this embodiment determines a parameter for successful wireless communication, based on motion information indicating a motion of a third region of the person 90 which is different from the first and second regions. The following describes the communication device according to this embodiment, mainly centering around differences from Embodiments 1 and 2.

Figure 6:
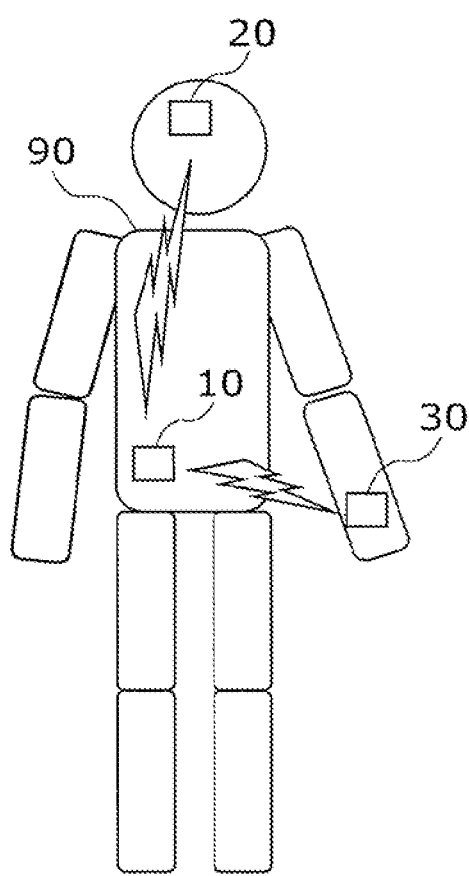
FIG. 6 is a diagram showing an overview of a communication system according to Embodiment 3 of the present invention.

FIG. 6 is a diagram showing an overview of a communication system 1 according to Embodiment 3 of the present invention. As shown in FIG. 6, the communication system 1 includes a motion measuring device 30 in addition to the communication device 10 and the communication partner device 20.

The motion measuring device 30 is attached to the third region, and measures the motion of the third region. The third region is one of the regions of the person 90, and is different from the first and second regions.

It is to be noted that, in this embodiment, the motion of the third region significantly influences the radio propagation environment between the communication device 10 and the communication partner device 20. In other words, the radio propagation environment depends on the motion of the third region. For instance, the first, second, and third regions are the head, lower back, and arm regions, respectively.

Figure 7:
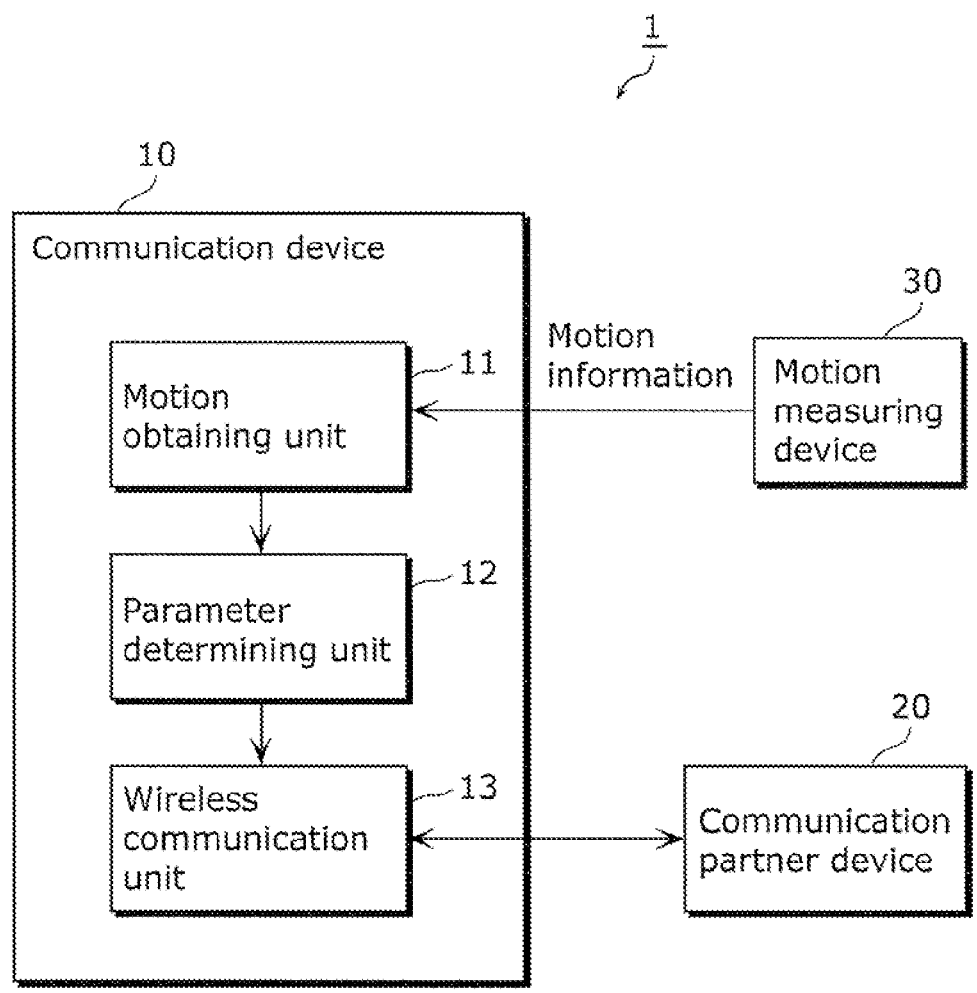
FIG. 7 is a block diagram showing a functional configuration of the communication system according to Embodiment 3 of the present invention.

FIG. 7 is a block diagram showing a functional configuration of a communication system 1 according to Embodiment 3 of the present invention. The wireless communication unit 13 in FIG. 7 is the same as in FIG. 2, and thus a description thereof is omitted. In addition, each type of operation performed by the communication device 10 is the same as in FIG. 4, and thus a diagrammatic representation and description thereof are omitted.

The motion obtaining unit 11 obtains, from the motion measuring device 30, information indicating the motion of the third region as motion information. More specifically, the motion obtaining unit 11 obtains, through wireless communication, the information indicating the motion of the third region which is measured by the motion measuring device 30, from the motion measuring device 30.

The parameter determining unit 12 determines a parameter corresponding to the motion indicated by the motion information obtained by the motion obtaining unit 11, using parameter information. In this embodiment, the parameter information is information in which the motion of the third region and the parameter are associated with each other. In other words, the parameter determining unit 12 determines a parameter adapted to a current or future radio propagation environment, by taking advantage of the significant influence of the motion of the third region on the radio propagation environment.

As described above, the communication device 10 according to this embodiment makes it possible to determine the parameter indicating a communication mode for successful wireless communication between the communication device 10 and the communication partner device 20, based on the motion of the third region influencing the radio propagation environment between the communication device 10 and the communication partner device 20. Therefore, when the motion of the third region to which the motion measuring device 30 is attached influences the radio propagation environment, the communication device 10 makes it possible to effectively determine the parameter adapted to the current or future radio propagation environment. In addition, the communication device 10 increases the reliability in wireless communication by performing wireless communication according to the parameter thus determined, and makes it possible to reduce the wireless communication power consumption.

Next, Embodiments 4 to 6 describe specific examples in the case where the communication systems according to Embodiments 1 to 3 are applied to biological information measuring systems.

Embodiment 4

Figure 8:
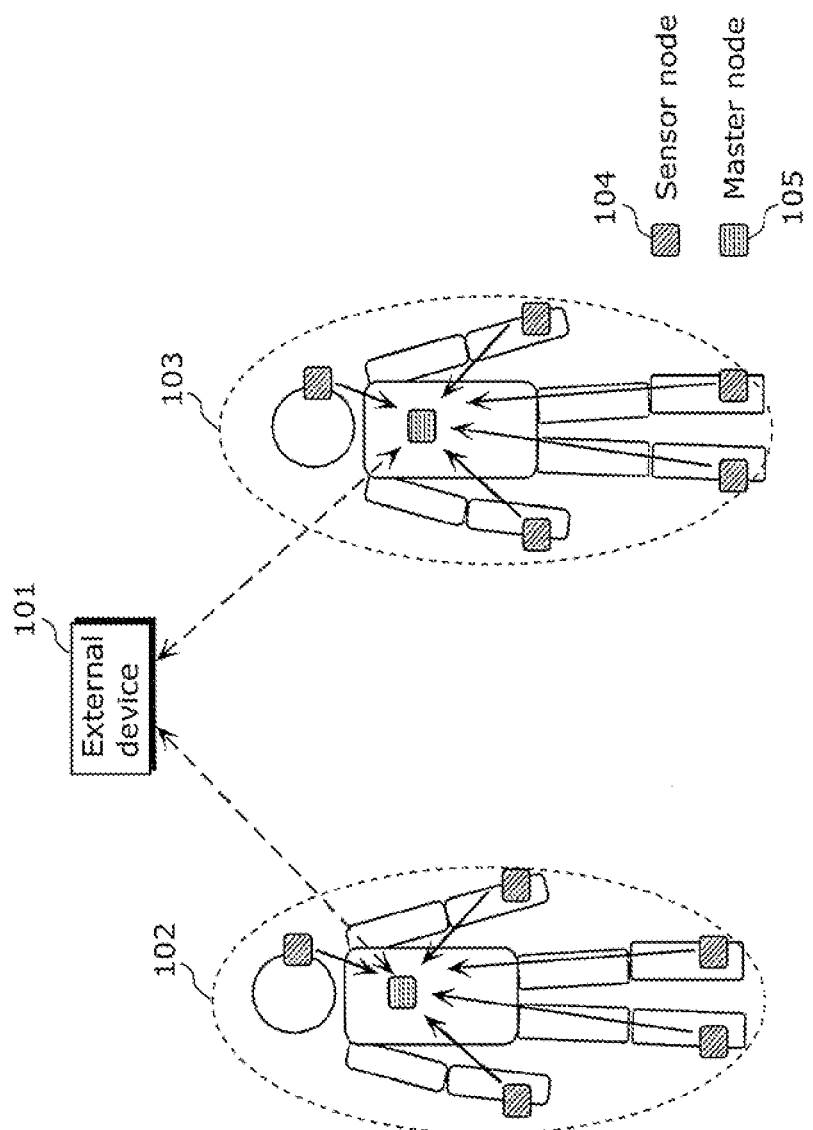
FIG. 8 is a diagram showing a configuration of a biological information measuring system according to Embodiment 4 of the present invention.

FIG. 8 is a diagram showing a configuration of a biological information measuring system according to Embodiment 4 of the present invention.

As shown in FIG. 8, the biological information measuring system includes: an external device 101 which collects biological information; a first network 102 formed on a first living body; and a second network 103 formed on a second living body. Each of the first and second networks 102 and 103 includes sensor nodes 104 and a master node 105.

Each of the sensor nodes 104 is attached to one of regions of a living body, and senses biological information (e.g., heartbeat, cardiac electric activity, pulse, myoelectric activity, brain wave, blood oxygen saturation level, blood sugar level, blood pressure, body temperature, posture, and acceleration). In addition, the sensor node 104 transmits the sensed biological information to the master node 105. In this embodiment, the sensor node 104 corresponds to the communication device 10.

The master node 105 receives, from each of the sensor nodes 104 belonging to the same network, the biological information sensed by sensor node 104. The master node 105 then performs biological information measurement by, for example, storing, analyzing, displaying, and outputting the biological information. Moreover, the master node 105 is connected to the external device 101 through wireless communication, and transmits, to the external device 101, a measurement result managed by the master node 105. In this embodiment, the master node 105 corresponds to the communication partner device 20.

The external device 101 provides a user or an operator service (e.g., healthcare and management of a medical condition) based on the measurement result received from the master node 105.

In FIG. 8, an independent network (the first network 102 or the second network 103) is formed for each living body to be measured. Each network includes at least one master node 105 and at least one sensor node 104. The number of the sensor nodes 104 to be attached or a region to which the sensor node 104 is to be attached can be determined depending on a type of biological information to be obtained.

A configuration within the network may be a star type in which the master node 105 that is pre-set centrally manages the sensor nodes 104 or a mesh type in which the master node 105 manages the sensor nodes 104 in a decentralized manner like an ad hoc network. In this embodiment, it is assumed that a node which interacts directly with the operator or the external device 101 is the master node 105, and that a node which transmits sensed biological information to the master node 105 is the sensor node 104.

Figure 10:
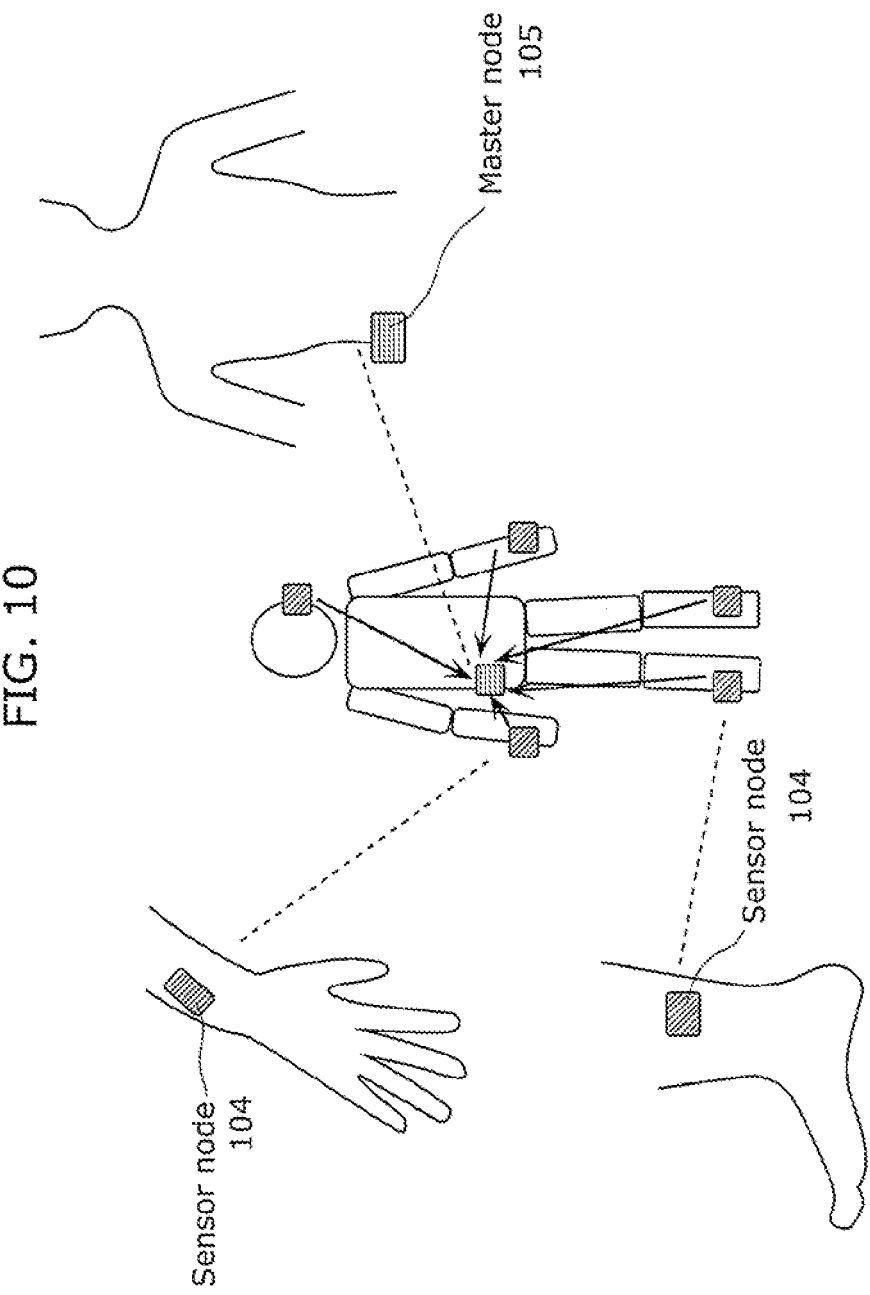
FIG. 10 is a diagram showing an exemplary use scene (attachment example) of sensor nodes and a master node.

FIG. 9A is a schematic diagram showing a hardware configuration of the sensor node 104 according to Embodiment 4 of the present invention. Moreover, FIG. 9B is a schematic diagram showing a hardware configuration of the master node 105 according to Embodiment 4 of the present invention. FIG. 10 is a diagram showing an exemplary use scene (attachment example) of the sensor nodes 104 and the master node 105. It is to be noted that the sensor node 104 and the master node 105 according to the present invention are not limited to the examples shown in FIGS. 9A and 9B. In addition, the use scene of the sensor nodes 104 and the master node 105 according to the present invention is not limited to the example shown in FIG. 10.

In FIG. 9A, the sensor node 104 includes a power supply unit 202, an acceleration sensor 203, a biological sensor 204, a wireless communication unit 205, an antenna 206, a microcomputer (microprocessor) 207, and a living-body-attached part 208. Electric power supplied from a coin battery 201 provided to the sensor node 104 is converted by the power supply unit 202 into a voltage or electric current necessary for driving each device (e.g., the acceleration sensor 203).

The acceleration sensor 203 measures three-dimensional acceleration of the sensor node 104. The biological sensor 204 measures, for instance, biological information such as a waveform of myoelectric activity of a region to which electrodes of the living-body-attached part 208 are attached.

The microcomputer 207 controls each device. Information measured by each sensor is transmitted to the master node 105 via the wireless communication unit 205 and the antenna 206.

In FIG. 9B, the master node 105 includes a display operation unit 209 and an external communication unit 210 in addition to the devices included in the sensor node 104 shown in FIG. 9A. The master node 105 obtains the biological information wirelessly transmitted from the sensor node 104, in addition to biological information measured by the biological sensor 204 included therein.

The display operation unit 209 presents the obtained biological information to the operator. More specifically, the display operation unit 209 is, for instance, a display device which displays a measurement value on a screen or an LED (Light Emitting Diode) for indicating a measurement state. In addition, the display operation unit 209 outputs various information according to an operation (e.g., an operation for instructing to start or end measurement by a switch or an operation for switching display) by the operator.

The external communication unit 210 communicates with the external device 101. It is to be noted that the external device 101 is typically a computer that is not attached to a living body but is put in place.

It is to be noted that although FIGS. 9A and 9B each show the only one biological sensor 204, the number of the biological sensors 204 may be plural.

As shown in FIG. 10, the sensor nodes 104 and the master node 105 may be directly attached to measurement regions of the living body or indirectly attached to the same using an attachment tool (not shown). In the example shown in FIG. 10, the master node 105 is attached to the lower back, and the sensor nodes 104 are attached to both of the wrists, both of the ankles, and the head region.

As stated above, the sensor node 104 and the master node 105 are attached to the living body, and thus are required to be compact. In addition, the sensor node 104 and the master node 105 are required to be battery-driven so that a movement of the living body is not encumbered with.

In other words, the sensor node 104 and the master node 105 are required to be driven by a compact battery having a small power source capacity. For this reason, the sensor node 104 and the master node 105 are required to consume power as little as possible so that measurement can be performed for a long period of time.

Moreover, downsizing the sensor node 104 and the master node 105 requires downsizing of the antenna 206. However, there is a case where downsizing the antenna reduces gain, because a sufficient size of the antenna for wavelength cannot be obtained. Furthermore, in order to avoid influence of electromagnetic waves on the living body, transmission power of the wireless communication unit 205 is required to be as low (small) as possible. The living body is a dielectric containing a lot of moisture, and thus a propagation loss occurs when shielding between nodes or the like is caused by the living body. Moreover, communication is performed at a distance shorter than a wavelength in a frequency band to be used, depending on the frequency band. Therefore, there occurs a case where radio propagation characteristics near the living body are different from common radio propagation characteristics in a common wide space.

For a better understanding of a description of operation, the following describes an example where the living body is a person.

Figure 11A:
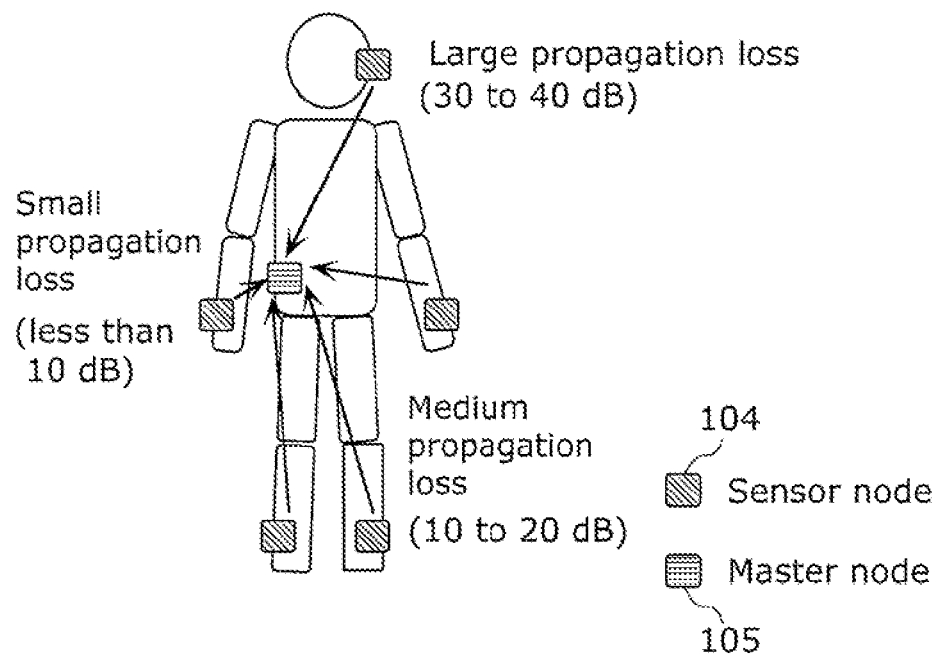
FIG. 11A is a diagram showing an example of radio propagation characteristics at a time when a living body stands upright and still.
Figure 11B:
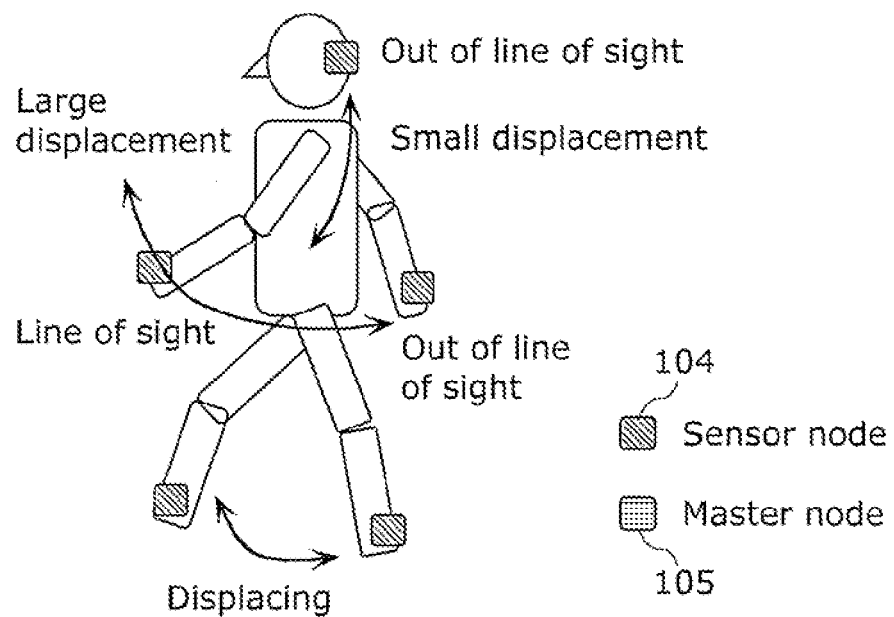
FIG. 11B is a diagram showing an example of radio propagation characteristics at a time when a living body is walking.

FIGS. 11A and 11B are diagrams each showing an example of radio propagation characteristics near the living body.

More specifically, FIG. 11A is a diagram showing an example of radio propagation characteristics at a time when the living body stands upright and still. FIG. 11B is a diagram showing an example of radio propagation characteristics at a time when the living body is walking. FIGS. 11A and 11B show the radio propagation characteristics between the master node 105 attached to the lower back region of the living body and the sensor node 104 attached to the head region, arm region, or leg region of the living body.

For instance, as shown in FIG. 11A, a propagation loss between the lower back region and the arm region, a close distance, becomes relatively small at the time when the living body stands upright and still. A propagation loss between the lower back region and the leg region, a short distance, becomes moderate. There is a tendency for a propagation loss to increase at the head region from which a distance to the lower back region is substantially the same as the distance between the lower back region and the leg region, because of shielding or the like by the arm (shoulder) region.

Furthermore, in addition to the static propagation losses by these regions, when the living body moves, a variation in radio propagation characteristics (change of a radio propagation environment) is caused by displacement of the regions for attachment. The walking movement shown in FIG. 11B is described as an example.

A person widely swings arm regions back and forth in walking movement. When one of the arm regions is positioned before a body of the person, a lower back region and the arm region of the person are in the line of sight. In contrast, when the arm region is positioned behind the body, the lower back region and the arm region are out of the line of sight, because the lower back region and the arm region are blocked by a trunk region of the person. Moreover, a distance to the lower back region is near around a side of the body, and thus a relative relationship between the lower back region and the arm region changes significantly.

Furthermore, the leg region causes vertical displacement in addition to a back and forth swing, at the time of walking. Just like the arm region, a relative relationship between the leg region and the lower back region (in the line of sight or out of the line of sight) changes between a case where the leg region is positioned before the body and a case where the leg region is positioned behind the body. It is to be noted that the distance between the leg region and the lower back region is greater than a distance between the arm region and the lower back region, and thus the relative relationship between the leg region and the lower back region changes less than the relative relationship between the arm region and the lower back region.

Although the head region of the person causes little displacement, the head region becomes in or out of the line of sight depending on a motion of the arm (shoulder) region that is a shield between the head region and the lower back region, and a relative relationship between the head region and the lower back region is varied.

The motions of these regions have relevance to each other. For example, in natural walking movement, when a right arm region and a left leg region of the person are positioned before the body, a left arm region and a right leg region of the person are positioned behind the body. Moreover, there is a limit to a range of motion of each of the regions.

Figure 12:
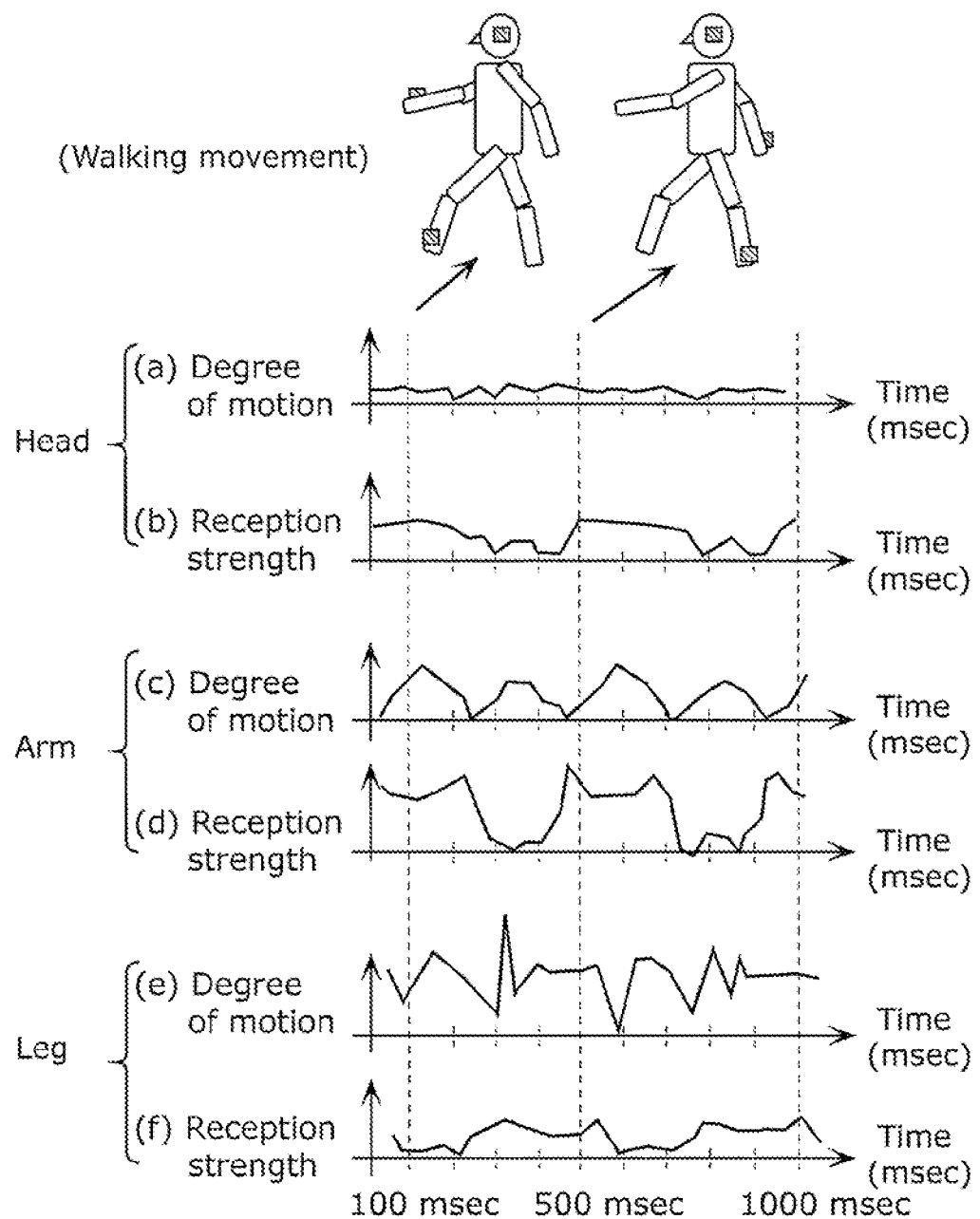
FIG. 12 is a diagram showing an example of radio propagation characteristics between a sensor node attached to respective regions and a master node attached to a lower back region at a time of walking.

FIG. 12 is a diagram showing an example of radio propagation characteristics between a sensor node attached to respective regions and a master node attached to a lower back region at a time of walking. The horizontal axis of each graph in FIG. 12 indicates a time (msec). The vertical axis of (a) in FIG. 12 shows an example of a degree of motion, and the vertical axis of (b) in FIG. 12 shows reception strength of a head region. Similarly, the vertical axis of (c) in FIG. 12 shows an example of a degree of motion, and the vertical axis of (d) in FIG. 12 shows an example of reception strength of an arm region. The vertical axis of (e) in FIG. 12 shows an example of a degree of motion, and the vertical axis of (f) in FIG. 12 shows an example of reception strength of a leg region.

A schematic view of postures at the time of walking which match times indicated by the horizontal axes is shown above the graphs. For instance, as shown in the schematic view, when a person is walking at a rate of about two steps per second, a right arm region and a left leg region of the person are positioned before a lower back region of the person at the time of 100 msec, and a left arm region and a right leg region of the person are positioned before the lower back region at the time of 500 msec.

Here, magnitude of acceleration obtained from the acceleration sensor is used as the degree of motion. It is to be noted that, for example, an average of magnitude of acceleration at respective axes obtained from a three-axis acceleration sensor may be used as the degree of motion. Furthermore, it is preferred to use a direction of motion in addition to the degree of motion.

In FIG. 12, although the sensor node attached to the head region shows a little variation in motion, it is clear that the reception strength varies according to the walking rate. Likewise, although the sensors attached to the arm region and the leg region each show a variation in reception strength, a time series waveform of the degree of motion significantly differs between the sensors attached to the arm region and the leg region, because a motion differs between the arm region and the leg region. Moreover, a change of a positional relationship with the master node attached to the lower back region differs from region for attachment to region for attachment, and thus a time lag occurs in a variation in reception strength.

Figure 13:
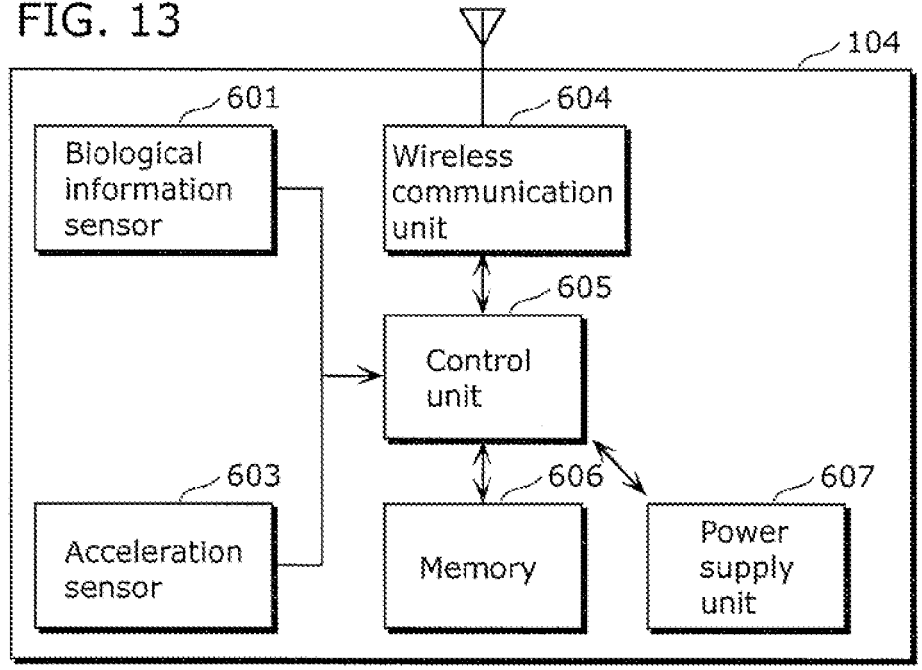
FIG. 13 is a block diagram showing a functional configuration of the sensor node according to Embodiment 4 of the present invention.

FIG. 13 is a block diagram showing a functional configuration of the sensor node 104 according to Embodiment 4 of the present invention. In FIG. 13, the sensor node 104 includes a biological information sensor 601, an acceleration sensor 603, a wireless communication unit 604, a control unit 605, a memory 606, and a power supply unit 607.

The biological information sensor 601 is an example of a moving body information sensor, and measures biological information of a region to which the sensor node 104 is attached. It is to be noted that the biological information sensor 601 may measure various types of biological information. The number of the types of biological information measured by the biological information sensor 601 may be determined according to a region for attachment or biological information of which measurement is desired. For instance, the biological information sensor 601 may include a body temperature sensor and a pulse sensor. Moreover, for instance, the biological information sensor 601 may include a myoelectric activity sensor, a blood oxygen saturation level sensor, and the body temperature sensor.

It is to be noted that a communication device according to an implementation of the present invention includes biological information sensors in advance, and may select only necessary biological information sensors from among the biological information sensors and use the selected biological information sensors, when used (attached).

The acceleration sensor 603 corresponds to a motion obtaining unit, and measure three-dimensional acceleration. In other words, the acceleration sensor 603 makes it possible to measure the motion (posture or displacement (movement)) of the region to which the sensor node 104 is attached. It is to be noted that the sensor node 104 may include at least one of a posture sensor, a gyroscope, an angle sensor, an extension and flexion sensor, and a rotation sensor, in addition to or instead of the acceleration sensor.

The measurement information measured by the biological information sensor 601 and the acceleration sensor 603 is input to the control unit 605. The control unit 605 performs control (e.g., control of sensors, and correction of a sensing cycle or sensing information) necessary for obtaining biological information to be measured, and temporarily stores the measurement information in the memory 606. The control unit 605 reads out the temporarily stored measurement information from the memory 606, according to a communications protocol with the master node.

The wireless communication unit 604 transmits, through wireless communication, the measurement information read out by the control unit 605, to the master node 105.

Moreover, the control unit 605 performs control to cause the power supply unit 607 to enter a sleep mode so that power consumption is reduced as much as possible during a period that is not required for measurement or communication.

Furthermore, the control unit 605 serves as a parameter determining unit and a parameter generating unit. In other words, the control unit 605 determines a transmission parameter for wirelessly transmitting biological information to the master node 105, based on the acceleration measured by the acceleration sensor 603. Moreover, the control unit 605 creates a transmission parameter table in which a transmission parameter corresponding to signal strength of a radio signal received from the master node 105 and a motion of a region to which the sensor node 104 is attached are associated with each other, the motion being indicated by motion information obtained when the radio signal is received.

It is to be noted that the transmission parameter table is an example of parameter information. Moreover, the transmission parameter is an example of a parameter.

Figure 14:
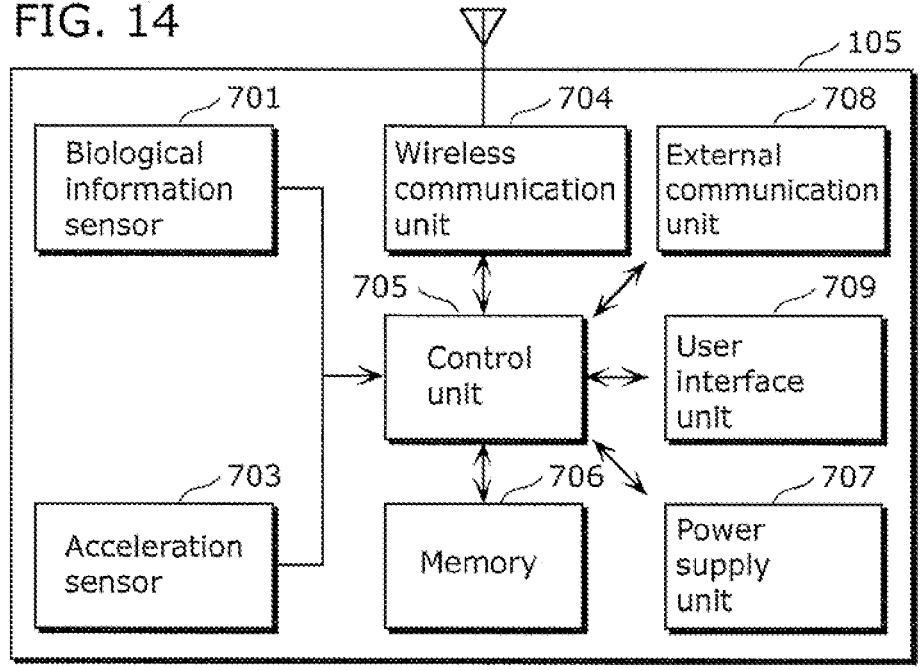
FIG. 14 is a block diagram showing a functional configuration of the master node according to Embodiment 4 of the present invention.

FIG. 14 is a block diagram showing a functional configuration of the master node 105 according to Embodiment 4 of the present invention. In FIG. 14, the master node 105 includes a biological information sensor 701, an acceleration sensor 703, a wireless communication unit 704, a control unit 705, a memory 706, a power supply unit 707, an external communication unit 708, and a user interface unit 709. It is to be noted that the constituent elements other than the external communication unit 708 and the user interface unit 709 included in the master node 105 have the same functions as those included in the sensor node 104 in FIG. 13, and thus a description of thereof is omitted.

The user interface unit 709 receives an input from an operator, and outputs information to the operator. The user interface unit 709 receives the input from the operator via, for instance, an input unit (not shown) such as a switch. More specifically, the user interface unit 709 receives an input such as an instruction to start or end measurement and an instruction to change a measurement mode. In addition, the user interface unit 709 outputs information indicating a measurement status or a measurement result via, for example, a display unit (not shown) such as a liquid crystal display and an LED, or an audio output unit (not shown) which outputs audio.

The external communication unit 708 transmits and receives information or data to and from the external device 101 not attached to a living body. For instance, the external communication unit 708 transmits, through wire or wirelessly, the biological information received from each of the sensor nodes 104. With this, each sensor node 104 does not need to communicate with the external device 101 located at a relatively far distance, and thus it becomes possible to reduce power consumption of the whole biological information measuring system.

It is to be noted that the above-mentioned sleep mode is a mode for reducing electric power consumed by the sensor node 104 or the master node 105, by causing the control unit 605 or 705 to suspend power supply to, for instance, the biological information sensor 601 or 701, the acceleration sensor 603 or 703, or the wireless communication unit 604 or 704 during a period not required for measurement or communication.

It is to be noted that the master node 105 and the sensor node 104 may be distinguished from each other based on a difference in motion, having the same configuration. Hereinafter, for ease of description, it is assumed that a sensor node principally measures and transmits biological information, and that a maser node principally receives the biological information transmitted from the sensor node.

The following describes in detail operation of the biological information measuring system performed by the sensor node 104 and the master node 105.

Figure 15:
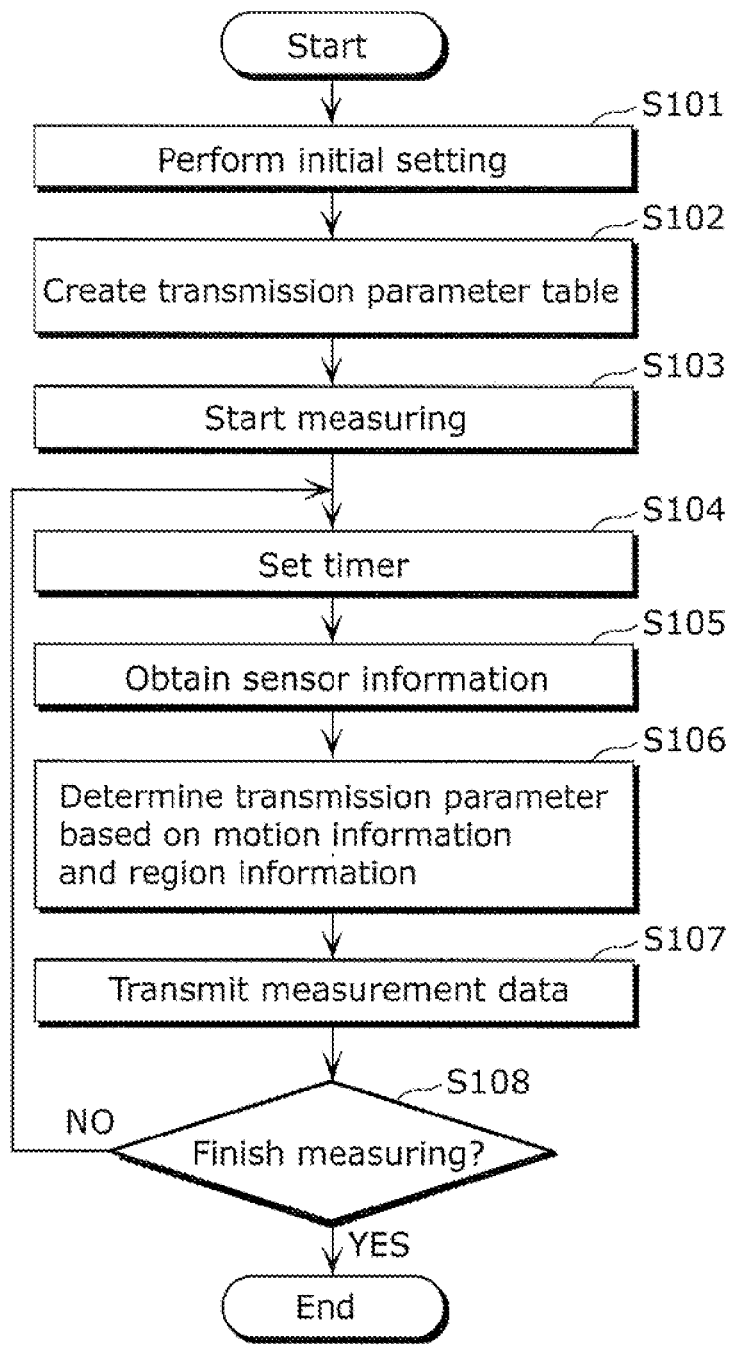
FIG. 15 is a flowchart showing operation of the sensor node according to Embodiment 4 of the present invention.

FIG. 15 is a flowchart showing operation of the sensor node 104 according to Embodiment 4 of the present invention.

When, the sensor node 104 is attached to a living body and a power switch thereof is pressed to ON, the sensor node 104 performs initial setting (S101).

The control unit 605 then creates a transmission parameter table corresponding to a radio propagation environment between a region to which the sensor node 104 is attached and a region to which a communication partner device is attached (S102). Here, a region for attachment may be determined for each node in advance, and a user may be instructed to attach the node to the region. Alternatively, each node may determine to which region the node is attached, based on a communication status, a motion state, or the like. Moreover, the transmission parameter table may be determined for each node in advance. Alternatively, each node may determine a transmission parameter most suitable for communication based on the communication status or motion state, and create or update the transmission parameter table.

Next, the master node 105 receives an instruction to start measurement from outside, and requests each node to start the measurement. The sensor node 104 starts the measurement according to the request to start the measurement from the master node 105 (S103).

Steps S104 to S108 form a basic loop for measurement. First, the sensor node 104 sets a timer based on a measurement cycle of biological information (S104). The sensor node 104 enters a sleep mode during a period not required for measurement and communication, and reduces power consumption.

When a timing for measurement comes, the biological information sensor 601 measures biological information and temporarily stores the measured biological information in the memory. Moreover, the acceleration sensor 603 measures acceleration as motion information (S105).

The control unit 605 then determines, with reference to the transmission parameter table, a transmission parameter corresponding to the motion information measured by the acceleration sensor 603 (S106). The transmission parameter includes a parameter indicating a communication mode such as modulation method, data rate, error-correction coding, transmission timing, transmission power, selective switching of antenna, directivity control, and selection of a relay route by a relay node.

After the transmission parameter adapted to a current radio propagation environment is determined, the control unit 605 reads out the biological information temporarily stored in the memory 606. The wireless communication unit 604 then transmits the read out information to the master node 105 according to the determined transmission parameter (S107).

The control unit 605 judges whether or not there is an instruction to end measurement (S108). Here, when there is no instruction to end measurement (No in S108), the flow returns to Step S104, and a measurement process is continued. On the other hand, when there is the instruction to end measurement (Yes in S108), the processing is terminated.

The following describes in detail the creation of the transmission parameter table in Step S102. Here, a case is described where the sensor node 104 attached to a first region of a living body creates a transmission parameter table in which a transmission parameter to be used for communication with the master node 105 attached to a second region of the living body is stored.

While the living body to which the sensor node 104 is attached is performing a predetermined movement (e.g., walking movement or traveling movement), the master node 105 transmits a sounding packet (radio signal). The control unit 605 stores, in the transmission parameter table, a transmission parameter corresponding to reception strength of the sounding packet and a measured degree of motion of the sensor node 104 in association with each other. In other words, the control unit 605 creates the transmission parameter table in which the transmission parameter corresponding to the signal strength of the received radio signal and the motion of the first region indicated by the motion information obtained when the radio signal is received are associated with each other.

The sensor node 104 makes it possible to determine, by using the transmission parameter table, a transmission parameter that is adapted to a variation in reception strength with the master node 105, which is predicted from a variation in degree of motion of the sensor node 104 caused by the movement of the living body. Thus, the sensor node 104 makes it possible to increase a success possibility of communication with the master node 105. To put it differently, the sensor node 104 makes it possible to increase the reliability in wireless communication.

Figure 16:
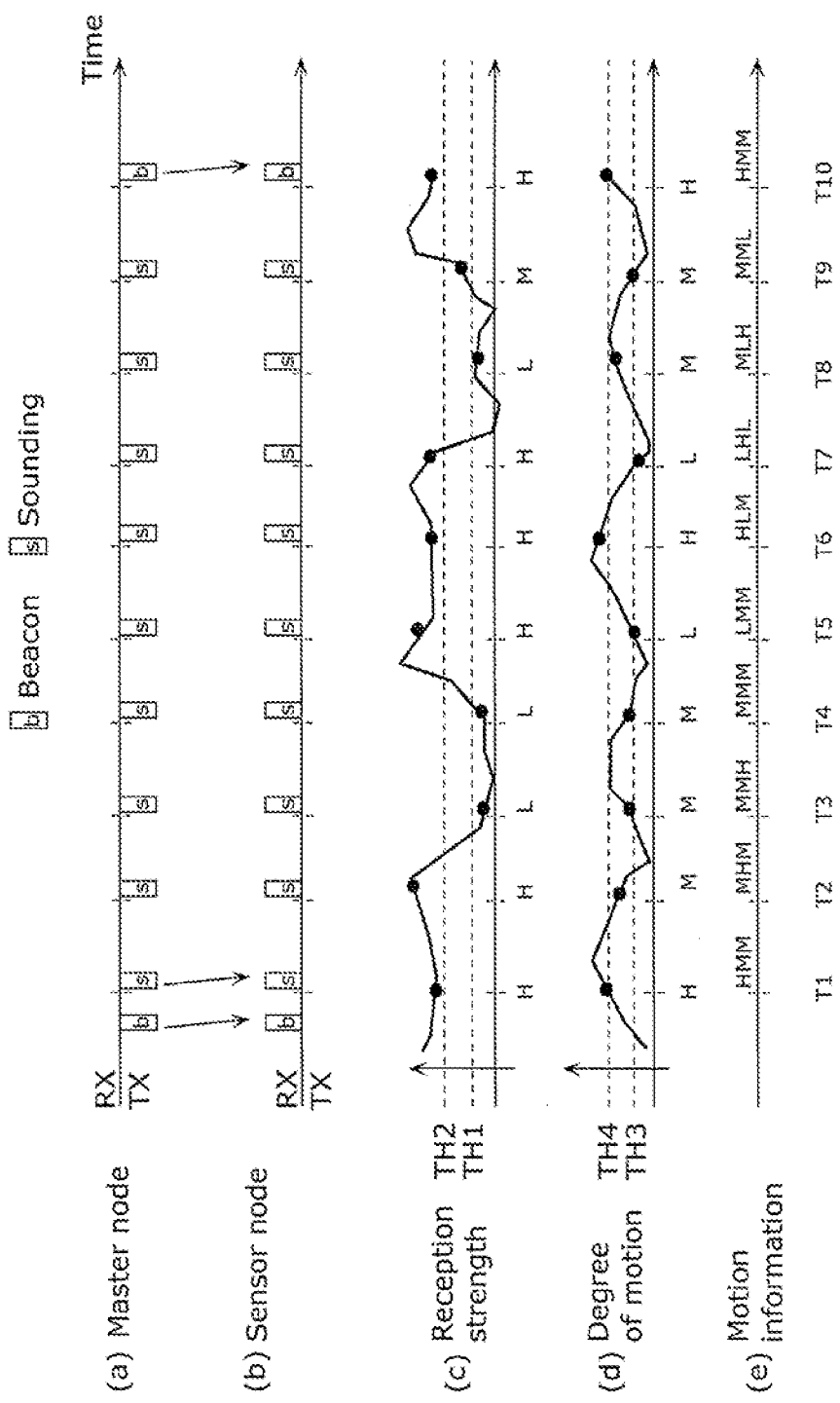
FIG. 16 is a diagram showing an exemplary sequence through which the sensor node creates a transmission parameter table according to Embodiment 4 of the present invention.

FIG. 16 is a diagram showing an exemplary sequence through which the sensor node 104 creates a transmission parameter table to be used for communication with the master node 105 according to Embodiment 4 of the present invention. More specifically, (a) in FIG. 16 shows a temporal variation in transmission and reception status of the master node 105. Here, "RX" denotes reception, and "TX" denotes transmission. A rectangle indicated by "b" denotes a beacon packet, and a rectangle indicated by "s" denotes a sounding packet. It is indicated here that the master node repeatedly transmits a beacon packet, and then transmits a sounding packet plural times at a predetermined interval. The beacon packet may include information such as a next-beacon transmission time, a transmission parameter table creation request, and a transmission time interval of a sounding packet. The sounding packet may include information such as a next-sounding packet transmission time and transmission power.

By using the same notations as in (a) in FIG. 16, (b) in FIG. 16 shows a temporal variation in transmission and reception status of the sensor node 104. It is indicated that the sensor node 104 receives the beacon packet and the sounding packet transmitted by the master node 105. The sensor node 104 which has received the sounding packet measures reception strength of the sounding packet, and stores the measured reception strength.

(c) in FIG. 16 shows an example of a variation in reception strength. It is assumed that the sound packet is transmitted at a fixed interval in an order of times T1 to T9. Hereinafter, time Tn (where n is an integer) is called a "time slot". In (c) in FIG. 16, reception strength at each reception timing is indicated by a black circle. A value of the reception strength may be stored as a true value or a decibel value. Alternatively, the value of the reception strength may be stored as a value representing a propagation loss obtained by subtracting reception power at a time of receiving a sounding packet from information of transmission power in the sounding packet.

Moreover, the value of the reception strength may be quantized and stored. For instance, as shown by (b) in FIG. 16, the value of the reception strength may be stored in the following manner. Threshold values TH1 and TH2 are determined, and the value is stored as "L", "M", or "H" when the value is less than TH1, equal to or greater than TH1 but less than TH2, or equal to or greater than TH2, respectively. In (c) in FIG. 16, the value of the reception strength is stored as a time series of HHLLHHHLMH in an order of times T1 to T9.

The sensor node 104 measures the degree of motion thereof almost concurrently with the measurement of the reception strength, and stores the measured degree of motion ((d) in FIG. 16). The value of the degree of motion may be an acceleration value or, for example, a value obtained by converting a value of integral of the acceleration or the like into a distance. Moreover, as shown by (d) in FIG. 16, the value of the degree of motion may be stored in the following manner. Threshold values TH3 and TH4 are determined, and the value is stored as "L", "M", or "H" when the value is less than TH3, equal to or greater than TH3 but less than TH4, or equal to or greater than TH4, respectively. In (d) in FIG. 16, the value of the degree of motion is stored as a time series of HMMMLHLMMH in an order of times T1 to T9.

In this way, the motion information is obtained from time series data of the measured degree of motion. The motion information can be obtained as, for instance, a time series pattern obtained by extracting a period dated back from a current time. In (e) in FIG. 16, the motion information is information collectively including degrees of motion for three time slots. Motion information at time T3 in (e) in FIG. 16 is indicated by MMH which is a combination of degrees of motion for past two time slots (T1 and T2) and a degree of current motion (T3). Similarly, MMM, LMM, HLM, LHL, MLH, or the like is obtained as motion information in each time slot.

The control unit 605 creates the transmission parameter table using the reception strength and the motion information thus obtained. FIG. 17 is a diagram showing an example of the transmission parameter table according to Embodiment 4 of the present invention. The motion information obtained in each time slot and a transmission parameter stored in association with each other in the transmission parameter table.

The transmission parameter is generated based on reception strength corresponding to motion information. For example, in the case of "L" indicating weak reception strength, a transmission parameter is generated which indicates that transmission timing is to be delayed until the reception strength becomes strong or that transmission is performed with an increase in transmission power. Here, transmission timing, transmission power, and retransmission timing are generated as transmission parameters.

It is to be noted that the transmission parameter can be generated in compliant with transmission and reception specifications of an implemented wireless communication unit. For instance, the transmission parameter may be a parameter for specifying a modulation method or a transmission rate so as to increase receiving sensitivity. Moreover, when spectrum spreading is directly used, the transmission parameter may be a parameter for specifying a spreading ratio. Alternatively, the transmission parameter may be a parameter for changing a pair of transmission and reception antennas by diversity.

For example, the first row of the transmission parameter table shown in FIG. 17 shows that reception strength indicates H (equal to or greater than the threshold value TH2) for motion information HMM. Transmission timing "now" indicating that transmission timing is immediate; transmission power "±0" indicating that transmission power needs no adjustment, and retransmission timing "now" indicating that retransmission timing is immediate are generated as transmission parameters corresponding to the reception strength H.

Moreover, the third row of the transmission parameter table shows that reception strength indicates L (less than the threshold value TH1) for motion information MMH. Transmission timing "delay" indicating that transmission timing is delayed, transmission power "H" indicating that transmission power is increased, and retransmission timing "2T" indicating that retransmission timing is after two time slots are generated as transmission parameters corresponding to the reception strength L.

Hereinafter, similarly, transmission timing, transmission power, and retransmission timing are generated based on the reception strength or time series information of the reception strength. When the sensor node 104 transmits biological information to the master node 105, the control unit 605 may select only one of the transmission parameters or a combination of the transmission parameters.

It is to be noted that the transmission parameter table may be created, as mentioned above, based on the movement of the living body to which the nodes are attached, each time the movement is started, or the transmission parameter table determined in advance based on average motion information or reception strength may be created. Moreover, although, for the sake of convenience of description, the example is described where the reception strength is stored in the transmission parameter table, the reception strength is not necessarily stored in the transmission parameter table.

The following describes steps S106 to S107 in which the sensor node 104 transmits, using the transmission parameter table, the biological information to the master node 105. Here, it is assumed that the sensor node 104 and the master node 105 are included in a measurement loop of the biological information, and that the living body to which the sensor node 104 is attached performs a movement that is almost the same as the predetermined movement performed at the time of creating the transmission parameter table. It is also assumed that the biological information is sensed in each time slot.

Figure 18:
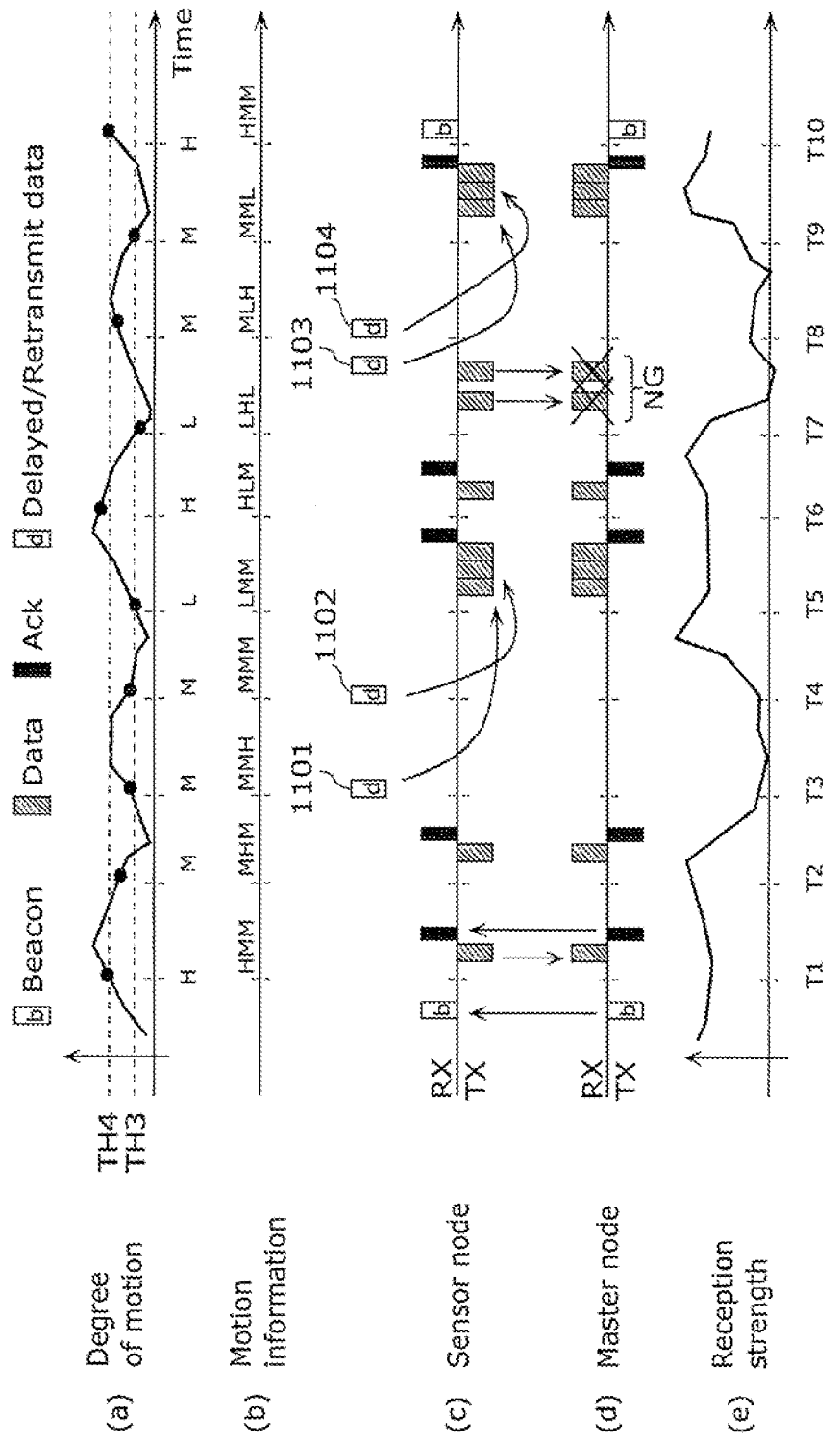
FIG. 18 is a diagram showing an exemplary sequence through which the sensor node transmits measurement data to the master node according to Embodiment 4 of the present invention.

FIG. 18 is a diagram showing an exemplary sequence through which the sensor node 104 transmits measurement data to the master node 105 according to Embodiment 4 of the present invention. More specifically, (a) in FIG. 18 shows a temporal variation in degree of motion of the sensor node 104. (b) in FIG. 18 shows a temporal variation of motion information obtained from the degree of motion measured by the sensor node 104. (c) in FIG. 18 shows a temporal variation in transmission and reception status of the sensor node 104. (d) in FIG. 18 shows a temporal variation in transmission and reception status of the master node 105. (e) in FIG. 18 shows a temporal variation in reception strength of the master node 105. Moreover, in (c) and (d) in FIG. 18, a rectangle indicated by "b" denotes a beacon packet, a hatched rectangle denotes a data packet, a black rectangle denotes an ACK packet, and a rectangle indicated by "d" denotes data to be delay-transmitted or retransmitted.

The master node 105 transmits a beacon packet at predetermined intervals. The beacon packet may include information such as a next-beacon transmission time, a biological information measurement request, a biological information measurement time interval, and a measurement data transmission interval.

The sensor node 104 measures, for each time slot, biological information and a degree of motion. The measured biological information (measurement data) is temporarily stored in the memory. Motion information shown by (b) in FIG. 18 is obtained from a time series variation in degree of motion shown by (a) in FIG. 18. For instance, motion information HMM is obtained at time slot T1.

The control unit 605 of the sensor node 104 selects, with reference to the transmission parameter table shown in FIG. 17, a transmission parameter for successful wireless communication at reception strength H estimated when the motion information indicates HMM. In other words, the control unit 605 determines, with reference to the transmission parameter table, the transmission parameter corresponding to the motion information HMM.

For example, the control unit 605 determines, at the time slot T1, a parameter indicating immediate transmission (now) as the transmission parameter corresponding to the motion information HMM. As shown by (c) in FIG. 18, the wireless communication unit 604 immediately transmits, to the master node 105, the measurement data stored in the memory as a data packet, according to the determined transmission parameter. Here, as shown by (e) in FIG. 18, the master node 105 has sufficiently high reception strength at the time slot T1. Thus, as shown by (d) in FIG. 18, the master node 105 successfully receives the data packet, and transmits an ACK packet. The control unit 605 of the sensor node 104 judges that the wireless communication has been successful, because the wireless communication unit 604 received the ACK packet, and makes it possible to control each processing unit so that the processing unit is in a sleep state until the next time slot.

Similarly, at time slot 12, the control unit 605 determines, with reference to the transmission parameter table, a parameter indicating immediate transmission (now) as a transmission parameter corresponding to motion information MHM. In addition, the wireless communication unit 604 immediately transmits measurement data according to the determined transmission parameter.

At time slot T3, motion information of the sensor node 104 indicates MMH. The control unit 605 determines, with reference to the transmission parameter table, a transmission parameter for successful wireless communication at reception strength L estimated when the motion information indicates MMH. In other words, the control unit 605 selects a transmission parameter indicating delay transmission (delay) as transmission timing or a transmission parameter indicating an increase in transmission power (H). Here, it is assumed that the control unit 605 selects the delay transmission (delay), and a transmission parameter indicating after two time slots (2T) as transmission timing. The control unit 605 stores measurement data 1101 at the time slot T3 in a transmission queue according to the transmission parameter thus selected, and makes it possible to control each processing unit so that the processing unit is in a sleep state until the next time slot.

Similarly, at time slot T4, the control unit 605 selects a transmission parameter indicating delay transmission (delay). Then, the control unit 605 stores measurement data 1102 at the time slot T4 in the transmission queue.

At time slot T5, motion information of the sensor node 104 indicates LMM. The control unit 605 determines, with reference to the transmission parameter table, a parameter indicating immediate transmission (now) as a transmission parameter corresponding to the motion information LMM. As a result, the wireless communication unit 604 transmits, to the master node 105, the measurement data 1101 and 1102 stored in the transmission queue and measurement data at the time slot T5.

Here, the wireless communication unit 604 may transmit the plural measurement data as respective data packets or one data packet. When the plural measurement data are transmitted as the one data packet, the wireless communication unit 604 may perform the transmission by concatenating the plural measurement data and through time-multiplexing, or perform the transmission through code-multiplexing using an orthogonal code such as the Walsh code or frequency-multiplexing using subcarriers.

As shown by (e) in FIG. 18, the master node 105 has sufficiently high reception strength at the time slot T5. Thus, as shown by (d) in FIG. 18, the master node 105 successfully receives the data packet, and transmits an ACK packet. The control unit 605 of the sensor node 104 judges that the wireless communication has been successful, because the wireless communication unit 604 received the ACK packet, and makes it possible to control each processing unit so that the processing unit is in a sleep state until the next time slot.

At time slot T6, the control unit 605 determines, with reference to the transmission parameter table, a parameter indicating immediate transmission (now) as a transmission parameter corresponding to motion information HLM. The wireless communication unit 604 immediately transmits measurement data according to the determined transmission parameter.

At time slot 17, the control unit 605 immediately transmits, with reference to the transmission parameter table based on motion information LHL, the measurement data. However, it is assumed that reception strength of the master node 105 is decreased at the time slot T7, at the point of transmitting a data packet. For this reason, the master node 105 fails to receive the data packet, and does not transmit the ACK packet.

In this situation, the control unit 605 judges that the wireless communication has been unsuccessful, because the wireless communication unit 604 of the sensor node 104 cannot receive the ACK packet. Here, the control unit 605 determines, with reference to the transmission parameter table shown in FIG. 17, retransmission timing (now) corresponding to the motion information LHL as a transmission parameter. Then, the wireless communication unit 604 performs retransmission within the time slot 17 according to the determined retransmission timing (now). When judging that a retransmission packet has not been successfully communicated, the control unit 605 stores measurement data 1103 in the transmission queue.

At time slot T8, the sensor node 104 selects delay transmission based on motion information MLH, and measurement data 1104 at the time slot T8 is stored in the transmission queue.

At time slot T9, motion information of the sensor node 104 indicates MML. The control unit 605 determines, with reference to the transmission parameter table, a parameter indicating immediate transmission (now) as a transmission parameter. With this, the wireless communication unit 604 transmits, to the master node 105, the measurement data 1103 and 1104 stored in the transmission queue and measurement data at the time slot T9.

It is to be noted that although each type of operation has been described above using as the example the case where the transmission parameter is the parameter for specifying the transmission timing, the transmission parameter is not necessarily the parameter for specifying the transmission timing. For instance, as shown in FIG. 17, the transmission parameter may be a parameter for specifying transmission power (radio wave strength in transmission). Even in this case, the wireless communication unit 604 makes it possible to perform wireless communication according to the parameter adapted to the current radio propagation environment, and thus it is possible to produce an effect of stably performing wireless communication.

Furthermore, the transmission parameter may be a transmission parameter obtained by combining the transmission parameter for specifying the transmission timing and the transmission parameter for specifying the transmission power. Moreover, a priority level is assigned to each of transmission parameters in advance, and, for example, the control unit 605 may select one of the transmission parameters according to the priority level. For instance, when a priority level assigned to the transmission parameter for specifying the transmission timing is higher than a priority level assigned to the transmission parameter for specifying the transmission power, the control unit 605 first selects the transmission parameter for specifying the transmission timing. When wireless communication performed according to the selected transmission parameter is unsuccessful, the control unit 605 then selects the transmission parameter for specifying the transmission power.

Moreover, the control unit 605 may select one of the transmission parameters according to an amount of data which is stored in a transmission queue and is to be transmitted. More specifically, for example, when data having an amount equal to or greater than a predetermined value is stored in the transmission queue, the control unit 605 may select the transmission parameter for specifying the transmission power. On the other hand, when only data having an amount less than the predetermined value is stored in the transmission queue, the control unit 605 may select the transmission parameter for specifying the transmission timing. With this, a lot of data is stored in the transmission queue, and it is possible to reduce delay in data transmission.

Furthermore, the control unit 605 may select one of the transmission parameters according to an amount of power that the power supply unit 607 can supply. More specifically, when the amount of power that can be supplied is equal to or greater than a predetermined value, the control unit 605 may select the transmission parameter for specifying the transmission power. On the other hand, when the amount of power that can be supplied is less than the predetermined value, the control unit 605 may select the transmission parameter for specifying the transmission timing. With this, it is possible to reduce the delay in transmission when the available power can be spared, and it is possible to reduce the power consumption when the available power cannot be spared.

It is to be noted that, just like the communication at the time slot T7, when it becomes clear that a judgment in the transmission parameter table is inconsistent with an actual communication status, the control unit 605 may update the transmission parameter table.

FIG. 19 is a diagram showing an example where the sensor node 104 updates the transmission parameter table according to Embodiment 4 of the present invention. As shown in FIG. 19, reception strength "H", transmission timing "now", transmission power "±0", and retransmission "now" are set in a row of the motion information LHL at the time slot 17. However, in the actual communication, a data packet and a retransmission packet both are not successfully communicated at the time slot 17, and are successfully communicated at the time slot T9 that is two time slots after the time slot 17. Thus, the control unit 605 makes it possible to update, using the result of the communication, the reception strength "H", the transmission timing "now", the transmission power "±0", and the retransmission "now" to reception strength "L", transmission timing "delay", transmission power "H", and retransmission "2T" in the row of the motion information LHL.

With this, the sensor node 104 makes it possible to dynamically create a transmission parameter table according to a current communication status. The sensor node 104 increases the reliability in wireless communication by determining a transmission parameter using the transmission parameter table thus created, and makes it possible to reduce the wireless communication power consumption.

It is to be noted that the control unit 605 may update the transmission parameter, table based on reception strength at a time when the sensor node receives the ACK packet from the master node 105. Moreover, the master node 105 may notify the sensor node 104 of the ACK packet including reception strength information of a data packet, and the control unit 605 may update the transmission parameter table using the notified reception strength information.

By repeating the above-mentioned processing, the sensor node 104 makes it possible to determine the transmission parameter adapted to the reception strength of the master node 105 which is estimated based on the motion information of the region to which the sensor node 104 is attached, and to transmit the measurement data to the master node 105 according to the determined transmission parameter.

As described above, the sensor node 104 according to this embodiment makes it possible to create the transmission parameter table to be used in determining the transmission parameter, using the signal strength of the radio signal actually received. In other words, the sensor node 104 makes it possible to dynamically create the transmission parameter table according to the actual dependence relationship between the motion of the region to which the sensor node 104 is attached and the radio propagation environment between the sensor node 104 and the master node 105. Therefore, the sensor node 104 increases the reliability in wireless communication by determining the transmission parameter using the transmission parameter table thus created, and makes it possible to reduce the wireless communication power consumption.

Embodiment 5

The following describes Embodiment 5 of the present invention.

In this embodiment, each of the sensor node 104 and the master node 105 creates a transmission parameter table, and determines a transmission parameter with reference to the created transmission parameter table. In other words, the control unit 705 of the master node 105 also serves as the parameter determining unit and the parameter generating unit. Hereinafter, each of the sensor node 104 and the master node 105 serves as a communication device as well as a communication partner device.

FIG. 20 is a diagram showing an exemplary sequence through which a transmission parameter table is created according to Embodiment 5 of the present invention. In FIG. 20, a black rectangle denotes an ACK packet, and other notations are the same as in those in FIGS. 16 and 18. The following describes, with reference to FIG. 20, processing in which each of the sensor node 104 and the master node 105 creates the transmission parameter table by the sensor node 104 transmitting a sounding packet plural times and the master node 105 acknowledging receipt of the sounding packet.

First, the master node 105 requests the sensor node 104 to perform sounding, by transmitting a beacon packet ((d) in FIG. 20). The sensor node 104 which has received the beacon packet starts sounding ((c) in FIG. 20).

The sensor node 104 obtains motion information ((b) in FIG. 20) by measuring, for each time slot, a degree of motion of the same ((a) in FIG. 20). The sensor node 104 includes the motion information for each time slot in a sounding packet, and transmits the sounding packet to the master node 105 ((c) in FIG. 20).

When receiving the sounding packet ((d) in FIG. 20), the master node 105 measures reception strength at the time of the reception, and stores the measured reception strength ((e) in FIG. 20). When receiving the sounding packet without error, the master node 105 transmits the ACK packet to the sensor node 104. Then, the master node 105 stores the received motion information of the sensor node 104, and the measured reception strength and a transmission parameter corresponding to the reception strength in association with each other in the transmission parameter table. In other words, the master node 105 (control unit 705) creates the transmission parameter table in which the transmission parameter corresponding to the signal strength of the received sounding packet and the motion which is indicated by the motion information included in the sounding packet and to which the sensor node 104 is attached are associated with each other. It is to be noted that the master node 105 may include the reception strength information of the sounding packet in the ACK packet, and transmit the ACK packet.

The sensor node 104 judges that the sounding packet has been successfully transmitted, when the ACK packet for the sounding packet is received within a predetermined time period. Then, the sensor node 104 stores the motion information of the same, and the result indicating the successful transmission and a transmission parameter corresponding to the result in association with each other in the transmission parameter table. Alternatively, the sensor node 104 may additionally store, in the transmission parameter table, reception strength measured at the time of receiving the ACK packet. Moreover, when the reception strength information of the sounding packet at the master node 105 is included in the ACK packet, the sensor node 104 may additionally store the reception strength information in the transmission parameter table.

For instance, in FIG. 20, at time slots T1 and T2, a sounding packet is successfully communicated, and an ACK packet is replied to the sensor node 104. Reception strength is low at time slot T3 ((e) in FIG. 20), and the master node 105 fails to receive the sounding packet (NG) ((d) in FIG. 20). In this case, the master node 105 cannot obtain motion information of the sensor node 104, and thus does not transmit an ACK packet. The master node 105 judges that the motion information of the sensor node 104 is indefinite, and stores the motion information and reception strength information at this time slot in association with each other in the transmission parameter table.

The sensor node 104 judges that the sounding packet has not been successfully transmitted, because the ACK packet cannot be received within a predetermined time period, and stores the motion information of the same and the result indicating the transmission failure in association with each other in the transmission parameter table. For example, FIG.

20 shows an example where, at time slots T3 and T4, a sounding packet is not successfully communicated, and an ACK packet is not replied.

By repeating the above-mentioned sequence a predetermined number of times, each of the sensor node 104 and the master node 105 makes it possible to create the transmission parameter table in which the motion of the region to which the sensor node 104 is attached to and the transmission parameter are associated with each other.

FIG. 21A is a diagram showing an example of the transmission parameter table created by the sensor node 104 according to Embodiment 5 of the present invention. FIG. 21B is a diagram showing an example of the transmission parameter table created by the sensor node 105 according to Embodiment 5 of the present invention.

As shown in FIG. 21A, the motion information of the sensor node 104 and a result of transmission indicating transmission success or failure are stored in association with each other in the transmission parameter table of the sensor node 104. Moreover, like in FIG. 17, the sensor node 104 stores a transmission parameter (transmission timing, transmission power, retransmission timing, or the like) based on the result of transmission in the transmission parameter table, in association with the motion information. Alternatively, the sensor node 104 may store a transmission parameter (especially a parameter for specifying transmission power) in the transmission parameter table, using reception strength information obtained from an ACK packet transmitted from the master node 105 at the time of transmission success.

Motion information received from the sensor node 104 and reception strength at the time of receiving the motion information are stored in association with each other in the transmission parameter table of the master node 105. Moreover, like in FIG. 17, the master node 105 stores a transmission parameter based on the reception strength in the transmission parameter table, in association with the motion information. In other words, the master node 105 creates a transmission parameter table in which a transmission parameter corresponding to signal strength (reception strength) of a received radio signal and a motion of a region (second region) which is indicated by motion information included in the radio signal and to which the sensor node 104 is attached are associated with each other.

Here, as shown by the third row (b) in FIG. 14, even when the sounding packet is not successfully received and the motion information of the sensor node 104 is not successfully received (indefinite is denoted by a x-mark), the master node 105 makes it possible to interpolate motion information using motion information included in sounding packets successfully received before and after the transmission failure. Furthermore, the master node 105 may notify information at the time when the communication is not successful, by transmitting, to the sensor node 104, the interpolated motion information and reception strength at the time of interpolation, using a beacon packet or the like.

Moreover, the master node 105 may hold transmission parameter tables for the sensor nodes 104, estimate timing at which the largest number of the sensor nodes 104 can be communicated, and transmit beacon packets with the timing.

In this case, the master node 105 first obtains motion information indicating a motion of each of regions to which the sensor nodes 104 are attached. Then, the master node 105 determines, for each of the sensor nodes 104, a communication timing at which wireless communication with the sensor node 104 is to be successful, with reference to a corresponding one of the transmission parameter tables. Furthermore, the master node 105 selects, from among the determined communication timings, a communication timing at which the largest number (determined number) of the sensor nodes 104 can be communicated, and determines a parameter for specifying the selected communication timing as a transmission parameter corresponding to the motion of the region.

The master node 105 transmits a transmission request for each sensor node 104 to transmit biological information, according to the transmission parameter thus determined. As a result, the maser node 105 makes it possible to perform simultaneous wireless communication with the sensor nodes 104 with the communication timings at which the wireless communication with the many sensor nodes 104 is highly likely to be successful. Therefore, the master node 105 and each sensor node 104 make it possible to effectively perform wireless communication, and reduce power consumption.

As stated above, in this embodiment, after creating the transmission parameter table for use in communication, each of the sensor node 104 and the master node 105 performs the wireless communication of the biological information in the same manner as described in FIG. 18.

As described above, the master node 105 according to this embodiment makes it possible to create the transmission parameter table to be used in determining the transmission parameter, using the signal strength of the radio signal actually received. In other words, the master node 105 makes it possible to dynamically create the transmission parameter table according to the actual dependence relationship between the motion of each of the regions to which the sensor nodes 104 are attached and the radio propagation environment between each of the sensor nodes 104 and the master node 105. Therefore, the master node 105 increases the reliability in wireless communication by determining the transmission parameter using the transmission parameter table thus created, and makes it possible to reduce the wireless communication power consumption.

Embodiment 6

The following describes Embodiment 6 of the present invention.

Like Embodiment 3, in this embodiment, a parameter for successful wireless communication between a communication device and a communication partner device is determined based on a motion of a first region to which the communication device is attached and a motion of a third region to which the communication partner device is attached, the third region being different from a second region. Hereinafter, a master node corresponds to the communication device, a first sensor node corresponds to a motion measuring device, and a second sensor node corresponds to the communication partner device.

Figure 22:
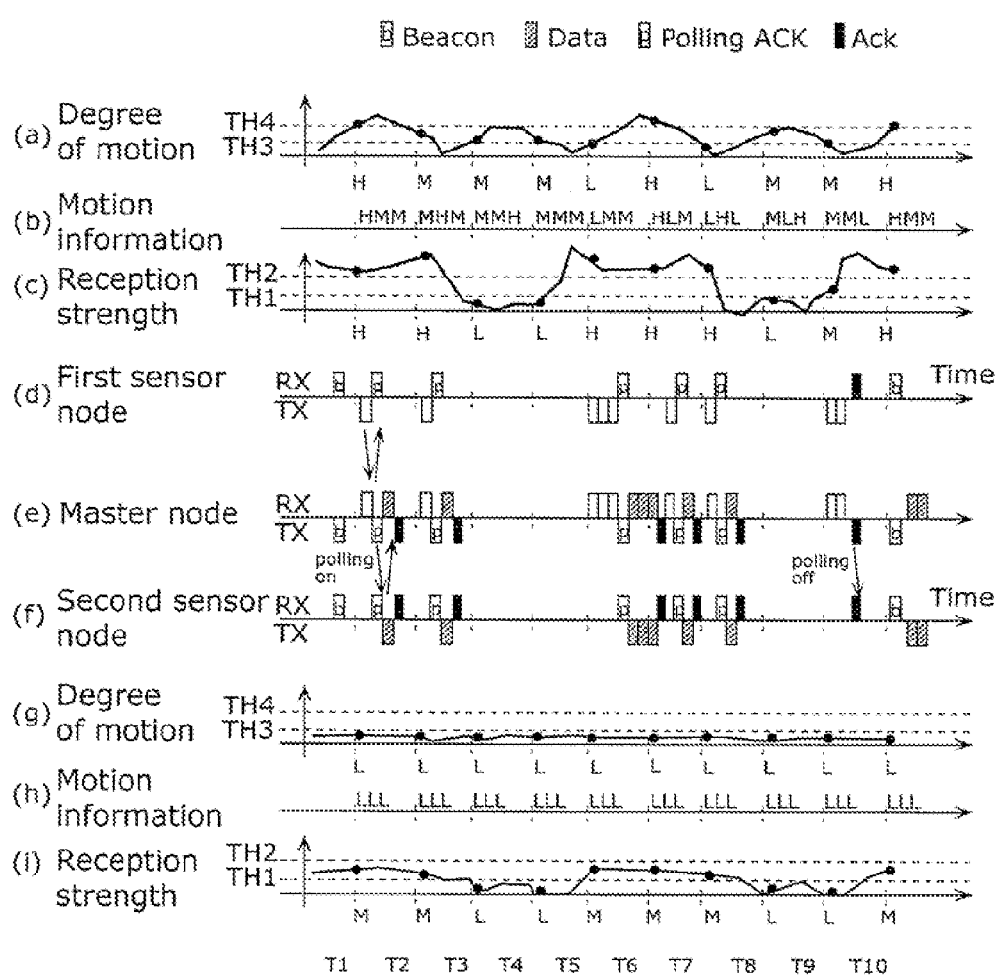
FIG. 22 is a diagram showing an exemplary sequence of wireless communication between two sensor nodes (a first sensor node and a second sensor node) and a master node according to Embodiment 6 of the present invention.

FIG. 22 is a diagram showing an exemplary sequence of wireless communication between two sensor nodes 104 (the first sensor node and the second sensor node) and the master node 105 according to Embodiment 6 of the present invention. More specifically, (a) in FIG. 22 shows a temporal variation in degree of motion of the first sensor node. (b) in FIG. 22 shows a temporal variation of motion information of the first sensor node. (c) in FIG. 22 shows a temporal variation in signal strength (reception strength) at the time when a radio signal transmitted from the first sensor node is received by the master node 105. (d) in FIG. 22 shows a temporal variation in transmission and reception status of the first sensor node. (e) in FIG. 22 shows a temporal variation in transmission and reception status of the master node 105. (f) in FIG. 22 shows a temporal variation in transmission and reception status of the second sensor node. (g) in FIG. 22 shows a temporal variation in degree of motion of the second sensor node. (h) in FIG. 22 shows a temporal variation of motion information of the second sensor node. (i) in FIG. 22 shows a temporal variation in signal strength (reception strength) at the time when a radio signal transmitted from the second sensor node is received by the master node 105.

The first sensor node and the second sensor node described here have the same configuration as the sensor nodes 104 according to Embodiments 4 and 5. In this embodiment, for the sake of convenience of description, the sensor nodes 104 are referred to as the first sensor node and the second sensor node for distinction.

Here, it is assumed that the first sensor node is attached to an arm region (the third region) of a living body, that the second sensor node is attached to a head region (the second region) of the living body, and that the master node 105 is attached to a lower back region (the first region) of the living body. In addition, it is assumed that the living body (e.g., a person) to which each node is attached is walking.

The arm region is swung back and forth in the walking movement, and thus a degree of motion measured by the first sensor node significantly varies ((a) in FIG. 22). Accordingly, reception strength of a radio signal which is transmitted from the first sensor node and received by the master node 105 also varies ((c) in FIG. 22).

In contrast, the head region hardly moves in the walking movement, and thus a degree of motion measured by the second sensor node does not vary much ((g) in FIG. 22). However, a motion of the arm region in the middle of a propagation path between the head region and the lower back region causes a variation in reception strength of a radio signal which is transmitted from the second sensor node and received by the master node 105 ((i) in FIG. 22).

In such a case, although there is a correlation between the degree of motion and the reception strength of the region to which the first sensor node is attached, there is no correlation between the degree of motion and the reception strength of the region to which the second sensor node is attached. Thus, the first sensor node makes it possible to determine an effective transmission parameter for successful wireless communication, based on motion information of the same (the first sensor node). However, the second sensor node does not make it possible to determine an effective transmission parameter for successful wireless communication, based on motion information of the same (the second sensor node).

In this embodiment, the master node 105 performs polling on the second sensor node based on the motion information of the first sensor node.

In (d), (e), and (f) in FIG. 22, a rectangle indicated by "b" denotes a beacon packet, a hatched rectangle denotes a data packet, a rectangle indicated by "p" denotes a polling ACK packet, and a black rectangle denotes an ACK packet.

Here, the polling ACK packet means a packet including information indicating ACK (Acknowledgment) or NACK (Negative Acknowledgment) for a node, and information indicating polling or no polling for another node.

For instance, when notifying the first sensor node and the second sensor node of reception success and a transmission request, respectively, the master node 105 transmits a polling ACK packet including information indicating [ACK (the first sensor node), polling (the second sensor node, ON)].

Moreover, when notifying the first sensor node and the second sensor node of reception success and a transmission pause, respectively, the master node 105 transmits a polling ACK packet including information indicating [ACK (the first sensor node), polling (the second sensor node, OFF)]. Alternatively, in this case, the master node 105 may transmit a regular ACK packet to the first sensor node.

Moreover, when notifying the first sensor node and the second sensor node of reception failure and a transmission request, respectively, the master node 105 transmits a polling ACK packet including information indicating [NACK (the first sensor node), polling (the second sensor node, ON)]. Alternatively, in this case, the master node 105 may transmit a packet for performing only polling on the second sensor node.

Moreover, when notifying the first sensor node and the second sensor node of reception failure and a transmission pause, respectively, the master node 105 transmits a polling ACK packet including information indicating [NACK (the first sensor node), polling (the second sensor node, OFF)]. Alternatively, in this case, the master node 105 may not have to transmit the polling ACK packet.

First, it is assumed that each node creates in advance a transmission parameter table through the sequence described in Embodiment 4 or 5. The master node 105 holds transmission parameter tables of the first sensor node and the second sensor node, stores motion information of the first sensor node and reception strength of the second sensor node in association with each other, based on a reciprocal relationship between the transmission parameter tables, and updates the transmission parameter table of the second sensor node.

In other words, the control unit 705 of the master node 105 creates a transmission parameter table in which a transmission parameter corresponding to the signal strength of a radio signal received from the second sensor node and the motion information included in a radio signal received from the first sensor node are associated with each other.

For example, the reception strength of the radio signal transmitted from the second sensor node indicates L at time slots T4, T5, T8, and T9 in FIG. 22. Here, the control unit 705 creates a transmission parameter table in which respective motion information MMH, MMM, MLH, and MML of the first sensor node and a transmission parameter indicating a communication mode for successful wireless communication at the reception strength L are associated with each other.

The following describes, in a temporal manner, a situation where the first sensor node and the second sensor node communicate with the master node 105, using the above-mentioned polling ACK packets and transmission parameter tables.

The master node 105 transmits, using broadcast, a beacon packet at time slot T1. Here, the beacon packet includes information for notifying the first sensor node to determine a transmission parameter based on the motion information of the first sensor node. Furthermore, the beacon packet includes information for notifying the second sensor node to determine a transmission parameter based on polling performed by the master node 105. With this, the first sensor node determines the transmission parameter at the time of data transmission, based on the motion information of the first sensor node. Moreover, the second sensor node determines the transmission parameter at the time of data transmission, based on the polling.

The first sensor node obtains the motion information HMM ((c) in FIG. 22) from a degree of motion of the first sensor node ((a) in FIG. 22) at time slot T2. Next, the first sensor node judges, with reference to the transmission parameter table of the first sensor node, that the reception strength indicates H in the case of the obtained motion information ((c) in FIG. 22), and determines a parameter indicating immediate transmission (now) as a transmission parameter corresponding to the reception strength H. Then, the first sensor node transmits, to the master node 105, a data packet including measurement data and the motion information HMM of the first sensor node, according to the determined transmission parameter ((d) in FIG. 22).

The master node 105 receives the data packet transmitted from the first sensor node, and obtains the measurement data and the motion information HMM of the first sensor node. Here, the master node 105 judges, with reference to the transmission parameter table of the second sensor node, that reception strength of the second sensor node which corresponds to the motion information of the first sensor node indicates M ((i) in FIG. 22), and determines a parameter indicating immediate transmission (now) as a transmission parameter corresponding to the reception strength M. As a result, the master node 105 notifies the first sensor node of ACK, and transmits, to the second sensor node, a polling ACK packet including information [ACK (the first sensor node), polling (the second sensor node, ON)] for notifying the second sensor node of a transmission request ((e) in FIG. 22). In other words, the master node 105 transmits, to the second sensor node, the transmission request for the second sensor node to immediately transmit biological information, according to the determined transmission parameter.

The first sensor node receives the polling ACK packet, and judges, based on the information indicating ACK (the first sensor node), that the data packet has been successfully transmitted.

The second sensor node receives the polling ACK packet, judges that information indicating polling (the second sensor node, ON) indicates a data packet transmission request, and transmits a data packet including measurement data and motion information LLL of the second sensor node ((h) in FIG. 22) ((f) in FIG. 22).

The master node 105 receives, through wireless communication, the data packet including the biological information measured by the second sensor node, from the second sensor node. Then, the master node 105 transmits, to the second sensor node, an ACK packet notifying reception success. The second sensor node receives the ACK packet, and judges that the data packet has been successfully transmitted.

A description of time slot T3 is omitted, because the same communication as in the time slot T2 is performed.

At time slots T4 and T5, the first sensor node judges, based on motion information of the same ((b) in FIG. 22), that reception strength indicates L ((c) in FIG. 22), and stores measurement data in the memory without transmitting the measurement data.

The master node 105 estimates motion information of the first sensor node at each of the time slots T4 and T5, based on histories of motion information of the first sensor node and the transmission parameter table of the first sensor node. For instance, the master node 105 estimates motion information of the first sensor node based on order of plural motion information of the first sensor node stored in the transmission parameter table. Then, the master node 105 determines, with reference to the transmission parameter table of the second sensor node, a transmission parameter corresponding to the estimated motion information of the first sensor node.

Here, it is assumed that the master node 105 estimates that the motion information of the first sensor node indicates MMH at the time slot T3 and the motion information of the first sensor node indicates MMM at the time slot T4. Then, the master node 105 judges, with reference to the transmission parameter table, that the reception strength of the second sensor node indicates L when the motion information indicates MMH and the motion information indicates MMM, and determines a parameter indicating delay transmission (delay) as the transmission parameter. With this, the master node 105 does not perform the polling on the second sensor node according to the determined transmission parameter.

The master node 105 does not perform the polling, and thus the second sensor node judges that the time slots T4 and T5 are not suitable for data packet transmission, and stores the measurement data in the memory.

At time slot T6, the first sensor node judges, based on motion information of the first sensor node ((b) in FIG. 22), that reception strength indicates H, and determines a parameter indicating immediate transmission (now) as a transmission parameter. Then, the first sensor node transmits, to the master node 105, a data packet including the measurement data of the respective time slots T4 and T5 stored in the memory, the measurement data of the time slot T6, and the motion information ((d) in FIG. 22). Like the time slot T2, the master node 105 transmits a polling ACK packet, and receives a data packet from the second sensor node.

A description of time slots T7 and T8 is omitted, because the same communication as in the time slot T2 is performed. In addition, a description of time slot T9 is omitted, because the same communication as in the time slot T4 is performed.

At time slot T10, the first sensor node transmits a data packet based on motion information of the first sensor node. The master node 105 judges, based on motion information MML ((b) in FIG. 22) of the first sensor node included in the received data packet, that reception strength of the second sensor node indicates L ((i) in FIG. 22), and determines a parameter indicating delay transmission (delay) as a transmission parameter. With this, the master node 105 transmits an ACK packet to the first sensor node without performing polling on the second sensor node. Alternatively, in this case, the master node 105 may transmit a polling ACK packet including information indicating [ACK (the first sensor node), polling (the second sensor node, OFF)].

As stated above, even when the motion information of the second sensor node and the reception strength of the radio signal transmitted from the second sensor node to the master node 105 are not associated with each other, the master node 105 makes it possible to create the transmission parameter table. In other words, the master node 105 makes it possible to create a transmission parameter table in which motion information of the first sensor node and a transmission parameter to be used for wireless communication between the second sensor node and the master node 105 are associated with each other. The master node 105 makes it possible to efficiently determine, with reference to the transmission parameter table thus created, a transmission parameter indicating a transmission method for successful wireless communication.

The master node 105 according to this embodiment makes it possible to create the transmission parameter table to be used in determining the transmission parameter, using the signal strength of the radio signal actually received. In other words, the master node 105 makes it possible to dynamically create the transmission table according to the actual dependence relationship between the motion of the region to which the first sensor node is attached and the radio propagation environment between the second sensor node and the master node 105. Therefore, the master node 105 increases the reliability in wireless communication by determining the transmission parameter using the transmission parameter table thus created, and makes it possible to reduce the wireless communication power consumption.

Although the communication device according to the implementation of the present invention has been described above based on the embodiments, the present invention is not limited to the embodiments. The scope of the present invention includes the embodiments to which various modifications conceived by a person with an ordinary skill in the art are made as well as other embodiments obtained by combining the constituent elements in different embodiments without departing from the gist of the present invention.

For example, although the communication device 10 determines the parameter based on the motion of the one of the first to third regions in Embodiments 1 to 3, the communication device 10 may determine a parameter based on a combination of the motions of the first to third regions. In this case, parameter information is information in which the combination of the motions of the first to third regions and the parameter are associated with each other.

With this, when a radio propagation environment depends on motions of regions, the communication device 10 makes it possible to effectively determine a parameter adapted to the radio propagation environment. In particular, when there is a possibility that the communication device 10 and the communication partner device 20 both move, it is possible to effectively determine the parameter.

Moreover, in Embodiment 5, the master node 105 efficiently creates the transmission parameter table based on the motion of the sensor node 104, by receiving, from the sensor node 104, the packet including the motion information in each time slot. However, the master node 105 does not necessarily have to create the transmission parameter table in the above manner. For instance, the master node 105 may receive, from the sensor node 104, the transmission parameter table created by the sensor node 104 as in Embodiment 4.

It is to be noted that each of the embodiments has been described using the example where the living body is the person. However, the living body does not have to be the person, and may be a living body (e.g., an animal other than the person) to which a sensor node and a master node can be attached. Alternatively, the sensor node or the master node does not have to be attached to the living body, and may be attached to, for example, a machine which performs a motion such as repeating, traveling, and the like. In other words, the sensor node or the master node may be attached to a moving body. In this case, the sensor node or the master node may include a moving body information sensor. The moving body information sensor may, for instance, measure, as moving body information, a state (wear status, an amount of lubricant, or the like) of a region of the moving body.

It is to be noted that each of the configurations according to the embodiments may be implemented as an integrated circuit, that is, LSI (Large Scale Integration). For example, the communication device 10 may be configured by a system LSI including the motion obtaining unit 11, the parameter determining unit 12, and the wireless communication unit 13. The LSIs may be integrated into one chip or into a single chip so as to include par or all of the LSIs.

Although the integrated circuit is referred to as the LSI, it may also be referred to as an IC (Integrated circuit), a system LSI, a super LSI, or an ultra LSI depending on a difference in a degree of integration. Moreover, a circuit integration method is not limited to the LSI, and may be realized with a dedicated circuit or a general-purpose processor. FPGA (Field Programmable Gate Array) that can be programmed after the manufacture of the LSI or a reconfigurable processor which can reconfigure connection or setting of circuit cells in the LSI may be used for the same purpose. Alternatively, computations of these functional blocks may be performed using, for instance, a DSP (Digital Signal Processor) or a CPU (Central Processing Unit). In addition, these processing steps may be recorded as a program on a recording medium, and processed by executing the program.

Furthermore, if integrated circuit technology that replaces the LSI appears through progress in semiconductor technology or other derived technology, that technology can naturally be used to carry out integration of the functional blocks. Application of biotechnology is one such possibility.

Moreover, the present invention can be realized not only as the communication device including such characteristic processing units but also as a communication method including, as steps, the characteristic processing units of the communication device. In addition, the present invention can be realized as a computer program causing a computer to execute each characteristic step included in the communication method. It goes without saying that such a computer program can be distributed via a non-transitory computer-readable recording medium such as a CD-ROM and a communication network such as the Internet.

INDUSTRIAL APPLICABILITY

A communication device according to an implementation of the present invention makes it possible to increase, when attached to one of regions of a moving body, reliability in wireless communication between the communication device and a communication partner device attached to another region of the moving body. With this, the communication device according to the implementation of the present invention attempts to extend service life of battery by reducing excessive power consumption, and thus is useful as a biological information measuring device which enables long-time constant measurement. In addition, the communication device according to the implementation of the present invention can be applied to a sensor network in which long-time use of the communication device is required in an environment where sensor nodes heavily move and accordingly a radio propagation environment varies.

REFERENCE SIGNS LIST

1 Communication system
10 Communication device
11 Motion obtaining unit
12 Parameter determining unit
13 Wireless communication unit
20 Communication partner device
30 Motion measuring device
101 External device
102 First network
103 Second network
104 Sensor node
105 Master node
201 Coin battery
202 Power supply unit
203 Acceleration sensor
204 Biological sensor
205 Wireless communication unit
206 Antenna
207 Microcomputer
208 Living-body-attached part
209 Display operation unit
210 External communication unit
601, 701 Biological information sensor
603, 703 Acceleration sensor
604, 704 Wireless communication unit
605, 705 Control unit
606, 706 Memory
607, 707 Power supply unit
708 External communication unit
709 User interface unit

The invention claimed is:

1. A communication device which performs, when attached to a first region of a moving body, wireless communication with a communication partner device attached to a second region of the moving body, said communication device comprising:
a motion obtaining unit configured to obtain motion information indicating a motion of at least one region of the moving body;
a parameter determining unit configured to determine a parameter corresponding to the motion of the region of the moving body indicated by the motion information obtained by said motion obtaining unit, using parameter information in which the motion and a parameter indicating a communication mode for successful wireless communication are associated with each other; and
a wireless communication unit configured to perform wireless communication with the communication partner device according to the parameter determined by said parameter determining unit,
wherein said motion obtaining unit is configured to obtain, as the motion information, information indicating a motion of the first region, and
the parameter information is information in which the motion of the first region and a parameter which corresponds to signal strength of a radio signal received from the communication partner device when the motion is measured and indicates the communication mode for successful wireless communication are associated with each other in advance.

2. The communication device according to claim 1,
wherein said wireless communication unit is configured to receive a radio signal from the communication partner device, and
said communication device further comprises a parameter generating unit configured to generate the parameter information in which a parameter corresponding to signal strength of the received radio signal and the motion of the first region indicated by the motion information obtained when the radio signal is received are associated with each other.

3. The communication device according to claim 1,
wherein the motion information is information indicating a temporal variation in magnitude of acceleration of the region of the moving body.

4. The communication device according to claim 1,
wherein the parameter includes at least one of a parameter for specifying communication timing and a parameter for specifying radio wave strength in transmission.

5. The communication device according to claim 1, further comprising
a moving body information sensor which measures moving body information of the first region,
wherein said wireless communication unit is configured to transmit, through wireless communication, the moving body information measured by said moving body information sensor, to the communication partner device.

6. The communication device according to claim 1,
wherein the communication partner device measures moving body information of the second region, and
said wireless communication unit is configured to receive, through wireless communication, the moving body information measured by the communication partner device.

7. The communication device according to claim 6,
wherein there is more than one communication partner device, and
said communication device further comprises an external communication unit configured to transmit, to an external device not attached to the moving body, the moving body information which said wireless communication unit has received from each of the communication partner devices.

8. A communication device which performs, when attached to a first region of a moving body, wireless communication with a communication partner device attached to a second region of the moving body, said communication device comprising:
a motion obtaining unit configured to obtain motion information indicating a motion of at least one region of the moving body;
a parameter determining unit configured to determine a parameter corresponding to the motion of the region of the moving body indicated by the motion information obtained by said motion obtaining unit, using parameter information in which the motion and a parameter indicating a communication mode for successful wireless communication are associated with each other; and
a wireless communication unit configured to perform wireless communication with the communication partner device according to the parameter determined by said parameter determining unit,
wherein said motion obtaining unit is configured to obtain, as the motion information, information indicating a motion of the second region, and
the parameter information is information in which the motion of the second region and the parameter are associated with each other.

9. The communication device according to claim 8,
wherein said wireless communication unit is configured to receive a radio signal including the motion information indicating the motion of the second region from the communication partner device, and
said communication device further comprises a parameter generating unit configured to generate the parameter information in which a parameter corresponding to signal strength of the received radio signal and the motion of the second region indicated by the motion information obtained when the radio signal is received are associated with each other.

10. A communication device which performs, when attached to a first region of a moving body, wireless communication with a communication partner device attached to a second region of the moving body, said communication device comprising:
a motion obtaining unit configured to obtain motion information indicating a motion of at least one region of the moving body;
a parameter determining unit configured to determine a parameter corresponding to the motion of the region of the moving body indicated by the motion information obtained by said motion obtaining unit, using parameter information in which the motion and a parameter indicating a communication mode for successful wireless communication are associated with each other; and
a wireless communication unit configured to perform wireless communication with the communication partner device according to the parameter determined by said parameter determining unit,
wherein a motion measuring device which measures a motion of a third region that is different from the first and second regions is attached to the third region, said motion obtaining unit is configured to obtain, as the motion information, information indicating the motion of the third region from the motion measuring device, and the parameter information is information in which the motion of the third region and the parameter are associated with each other.

11. The communication device according to claim 10, wherein said wireless communication unit is configured to receive a radio signal from the communication partner device, and a radio signal including motion information indicating the motion of the third region from the motion measuring device, and said communication device further comprises a parameter generating unit configured to generate the parameter information in which a parameter corresponding to signal strength of the radio signal received from the communication partner device and the motion information included in the radio signal received from the motion measuring device are associated with each other.

12. A communication method performed by a communication device which is attached to a first region of a moving body and performs wireless communication with a communication partner device attached to a second region of the moving body, said communication method comprising:

obtaining motion information indicating a motion of at least one region of the moving body;

determining a parameter corresponding to the motion of the region of the moving body indicated by the motion information obtained in said obtaining, using parameter information in which the motion and a parameter indicating a communication mode for successful wireless communication are associated with each other; and performing wireless communication with the communication partner device according to the parameter determined in said determining, wherein, in said obtaining, information indicating a motion of the first region is obtained as the motion information, and the parameter information is information in which the motion of the first region and a parameter which corresponds to signal strength of a radio signal received from the communication partner device when the motion is measured and indicates the communication mode for successful wireless communication are associated with each other in advance.

13. An integrated circuit which performs, when attached to a first region of a moving body, wireless communication with a communication partner device attached to a second region of the moving body, said integrated circuit comprising:

a motion obtaining unit configured to obtain motion information indicating a motion of at least one region of the moving body;

a parameter determining unit configured to determine a parameter corresponding to the motion of the region of the moving body indicated by the motion information obtained by said motion obtaining unit, using parameter information in which the motion and a parameter indicating a communication mode for successful wireless communication are associated with each other; and a wireless communication unit configured to perform wireless communication with the communication partner device according to the parameter determined by said parameter determining unit, wherein said motion obtaining is configured to obtain information indicating a motion of the first region as the motion information, and the parameter information is information in which the motion of the first region and a parameter which corresponds to signal strength of a radio signal received from the communication partner device when the motion is measured and indicates the communication mode for successful wireless communication are associated with each other in advance.

14. A non-transitory computer-readable recording medium for use in a computer, the recording medium having a computer program recorded thereon for causing the computer to execute the communication method according to claim 12.

* * * * *